United States Patent
Bulet et al.

(10) Patent No.: US 7,384,911 B2
(45) Date of Patent: Jun. 10, 2008

(54) PEPTIDES HAVING ANTIMICROBIAL PROPERTIES AND COMPOSITIONS CONTAINING THEM, NOTABLY FOR THE PRESERVATION OF FOODSTUFFS

(75) Inventors: Philippe Bulet, Vendenheim (FR); Cécile Thouzeau, Schiltigheim (FR); Yvon LeMaho, Hoenheim (FR)

(73) Assignee: Centre National de la Recherche Scientifique - CNRS (FR)

( * ) Notice: Subject to any disclaimer, the term of this patent is extended or adjusted under 35 U.S.C. 154(b) by 0 days.

(21) Appl. No.: 11/027,111

(22) Filed: Dec. 30, 2004

(65) Prior Publication Data

US 2005/0245437 A1 Nov. 3, 2005

Related U.S. Application Data

(63) Continuation of application No. PCT/FR03/02041, filed on Jul. 1, 2003.

(30) Foreign Application Priority Data

Jul. 1, 2002 (FR) .................................. 02 08207

(51) Int. Cl.
*A61K 38/16* (2006.01)
(52) U.S. Cl. .......................................................... 514/2
(58) Field of Classification Search .................... None
See application file for complete search history.

(56) References Cited

FOREIGN PATENT DOCUMENTS

WO    WO 02/09738 A1    2/2002

OTHER PUBLICATIONS

Tarver et al. "Enteric beta-defensin: molecular cloning and characterization of a gene with inducible intestinal epithelial cell expression associated with *Cryptosporidium parvum* infection." Infect. & Immun., 1998, 66, 1045-56.*
Bensch et al. "hBD-1: a novel beta-defensin from human plasma," FEBS Letters., 1995, 368, 331-5.*
Jean-Luc Dimarcq et al., *Cysteine-Rich Antimicrobial Peptides in Invertebrates*, Biopolymers, vol. 47, 1998, pp. 465-477.
Evelyne Bachère et al., *Penaeidins, antimicrobial peptides of shrimp; a comparison with other effectors of innate immunity*, Aquaculture, vol. 191, 2000, pp. 71-88.
Brian C. Schutte et al., *Discovery of five conserved β-defensin gene clusters using a computational search strategy*, PNAS, vol. 99, Feb. 19, 2002, pp. 2129-2133.

* cited by examiner

*Primary Examiner*—Cecilia Tsang
*Assistant Examiner*—Christina M. Bradley
(74) *Attorney, Agent, or Firm*—DLA Piper US LLP

(57) ABSTRACT

An isolated peptide including an amino acid sequence of formula (II):

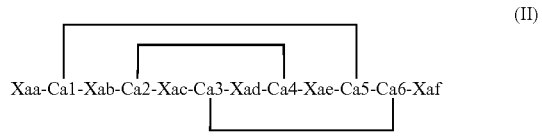

wherein Xaa is Ser-Phe-Gly-Leu, Xab is Arg-Leu-Arg-Arg-Gly-Phe, Xac is Ala-Xac2-Gly-Arg, Xad is Arg-Phe-Pro-Ser-Ile-Pro-Ile-Gly-Arg, Xae is Ser-Arg-Phe-Val-Gln, and Xaf is Arg-Arg-Val-Trp, Xac2 is histidine or arginine, Ca1, Ca2, Ca3, Ca4, Ca5 and Ca6 are sulfur containing amino acids, wherein each of Ca1-Ca5, Ca2-Ca4 and Ca3-Ca6 are linked together by a sulfur bridge, and wherein the amino acid sequence has antimicrobial activity.

9 Claims, 8 Drawing Sheets

Fig. 8

| β-DEFENSIN (SPECIES) | SEQUENCE OF THE MATURE PEPTIDE | PRINCIPAL SITES (ref.) |
|---|---|---|
| Spheniscin-1 (*Aptenodytes patagonicus*) | ...FGH... | Stomach content |
| Spheniscin-2 (*A. patagonicus*) | ...FGH... | Stomach content |
| Gallinacin-3 (*Gallus gallus*) | GTATQ...GSII... | L, T(1) |
| Gallopavin-1 (*Meleagris gallopavo*) | GTPIQ... | T(1) |
| HBD1 (*Homo sapiens*) | DHYN VSSG QLYSA PIFHKIQ TYRGKAK... | L, MB, GS (2) |
| HBD 2 (*H. sapiens*) | GIGDPVT LKSGAI HPVF PRRYKQ T GLPGTKQ KP | L, MB, GS, P, MP, T (2, 3, 4) |
| HBD 3 (*H. sapiens*) | LQKYY RV G R VLS LPKEEQ KGT GRK... | T, MB, P, GI (5, 6) |
| HBD 4 (*H. sapiens*) | ELDRI GYGTAR -KKK SQEYR DESLLNRTKP | E (7) |
| rhBD 1 (*Macaca mulatta*) | DHYN VRSG QLYSA PIYHRIQ T YHGKAK... | MP, GI (8) |
| rhBD 2 (*M. mulatta*) | GIGDPVT LKNGAI HPVF PRRYKQ T GLPGTKQ KP | MP, GI (8) |
| CBD 1 (*Pan troglodytes*) | DHYN VSSG QLYSA PIFHKIQ T YGGKAK... | MP, P (9) |
| CBD 3 (*P. troglodytes*) | GIINTLQKYY RV G R VLT LPKEEQ KT GRK... | P (10) |
| TAP (*Bos taurus*) | GVGNPVS VRNH I VPI SS T VG A... K | T (11) |
| LAP (*B. taurus*) | GVRNSQS RRNK I VPI PGSMRQ T LGAQ K | L (12) |
| EBD (*B. taurus*) | G NP S R NH I VPI PGNLRQ T TPS K WR | I (13) |
| MBD 1 (*M. musculus*) | QYK LQHG ISS PSNQLQ T KPDKPN KS | L, MP, O, T, TG, GI (14, 15) |
| MBD 2 (*M. musculus*) | AVGSLKSIGYEAELDA HTNCHY IV AI PPSARRP S FPEKNP TYMK | TG, T (16) |
| MBD 3 (*M. musculus*) | KKINNPVS LRKGR -WN IGNTRQ S GVP LK K | MP, GS (17) |
| MBD 4 (*M. musculus*) | QIINNPIT MTNGAI -W P PTAFRQ N GHPKIR... | L, O, T (18) |
| MBD 6 (*M. musculus*) | QLIN -PVT MSYG S QMS- NGGFRLG H GHPKIR... | O, L, T (19) |
| MBD 7 (*M. musculus*) | QDIN -KRA YREG L -LQ IGLFHK NF -4 KFQIPEKKTKIL | MP (20) |
| GBD 1 (*Capra hircus*) | --RRS HRNH VALT PRNMRQ T GPP H K | L, MP (21) |
| GBD 2 (*C. hircus*) | QGIINHRS YRL V APA PRNMRQ T HGPP K | GI (21) |
| SBD 1 (*Ovis. aries*) | QGVRNRL S HRNK VPS PRHMRQ T RGPP H K | T, GI (22) |
| SBD 2 (*O. orientalis aries*) | HGVTD --- RW K I VLT PGTMRQ T GGPB K | T, GI (22) |
| PBD 1 (*Sus scrofa*) | NIGN ---VS LRN VMP APKMKQ T GMPQ K | GI, MP (23) |

Arrangement of the disulfide bridges

SEQUENCE LISTING

<160> NUMBER OF SEQ ID NOS: 26

<210> SEQ ID NO 1
<211> LENGTH: 38
<212> TYPE: PRT
<213> ORGANISM: Aptenodytes patagonicus

<400> SEQUENCE: 1

Ser Phe Gly Leu Cys Arg Leu Arg Arg Gly Phe Cys Ala His Gly Arg
1               5                   10                  15

Cys Arg Phe Pro Ser Ile Pro Ile Gly Arg Cys Ser Arg Phe Val Gln
            20                  25                  30

Cys Cys Arg Arg Val Trp
        35

<210> SEQ ID NO 2
<211> LENGTH: 38
<212> TYPE: PRT
<213> ORGANISM: Aptenodytes patagonicus

<400> SEQUENCE: 2

Ser Phe Gly Leu Cys Arg Leu Arg Arg Gly Phe Cys Ala Arg Gly Arg
1               5                   10                  15

-continued

Cys Arg Phe Pro Ser Ile Pro Ile Gly Arg Cys Ser Arg Phe Val Gln
            20                  25                  30

Cys Cys Arg Arg Val Trp
            35

<210> SEQ ID NO 3
<211> LENGTH: 39
<212> TYPE: PRT
<213> ORGANISM: Gallus gallus

<400> SEQUENCE: 3

Gly Thr Ala Thr Gln Cys Arg Ile Arg Gly Gly Phe Cys Arg Val Gly
 1               5                  10                  15

Ser Cys Arg Phe Pro His Ile Ala Ile Gly Lys Cys Ala Thr Phe Ile
            20                  25                  30

Ser Cys Cys Gly Arg Ala Tyr
            35

<210> SEQ ID NO 4
<211> LENGTH: 39
<212> TYPE: PRT
<213> ORGANISM: Meleagris gallopavo

<400> SEQUENCE: 4

Gly Thr Pro Ile Gln Cys Arg Ile Arg Gly Gly Phe Cys Arg Phe Gly
 1               5                  10                  15

Ser Cys Arg Phe Pro His Ile Ala Ile Ala Lys Cys Ala Thr Phe Ile
            20                  25                  30

Pro Cys Cys Gly Ser Ile Trp
            35

<210> SEQ ID NO 5
<211> LENGTH: 36
<212> TYPE: PRT
<213> ORGANISM: Homo sapiens

<400> SEQUENCE: 5

Asp His Tyr Asn Cys Val Ser Ser Gly Gly Gln Cys Leu Tyr Ser Ala
 1               5                  10                  15

Cys Pro Ile Phe Thr Lys Ile Gln Gly Thr Cys Tyr Arg Gly Lys Ala
            20                  25                  30

Lys Cys Cys Lys
            35

<210> SEQ ID NO 6
<211> LENGTH: 41
<212> TYPE: PRT
<213> ORGANISM: Homo sapiens

<400> SEQUENCE: 6

Gly Ile Gly Asp Pro Val Thr Cys Leu Lys Ser Gly Ala Ile Cys His
 1               5                  10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40

<210> SEQ ID NO 7
<211> LENGTH: 40
<212> TYPE: PRT
<213> ORGANISM: Homo sapiens

<400> SEQUENCE: 7

```
Leu Gln Lys Tyr Tyr Cys Arg Val Arg Gly Gly Arg Cys Ala Val Leu
  1               5                  10                  15
Ser Cys Leu Pro Lys Glu Glu Gln Ile Gly Lys Cys Ser Thr Arg Gly
             20                  25                  30
Arg Lys Cys Cys Arg Arg Lys Lys
         35                  40
```

<210> SEQ ID NO 8
<211> LENGTH: 48
<212> TYPE: PRT
<213> ORGANISM: Homo sapiens

<400> SEQUENCE: 8

```
Glu Leu Asp Arg Ile Cys Gly Tyr Gly Thr Ala Arg Cys Arg Lys Lys
  1               5                  10                  15
Cys Arg Ser Gln Glu Tyr Arg Ile Gly Arg Cys Pro Asn Thr Tyr Ala
             20                  25                  30
Cys Cys Leu Arg Lys Trp Asp Glu Ser Leu Leu Asn Arg Thr Lys Pro
         35                  40                  45
```

<210> SEQ ID NO 9
<211> LENGTH: 36
<212> TYPE: PRT
<213> ORGANISM: Macaca mulatta

<400> SEQUENCE: 9

```
Asp His Tyr Asn Cys Val Arg Ser Gly Gly Gln Cys Leu Tyr Ser Ala
  1               5                  10                  15
Cys Pro Ile Tyr Thr Arg Ile Gln Gly Thr Cys Tyr His Gly Lys Ala
             20                  25                  30
Lys Cys Cys Lys
         35
```

<210> SEQ ID NO 10
<211> LENGTH: 41
<212> TYPE: PRT
<213> ORGANISM: Macaca mulatta

<400> SEQUENCE: 10

```
Gly Ile Gly Asp Pro Val Thr Cys Leu Lys Asn Gly Ala Ile Cys His
  1               5                  10                  15
Pro Val Phe Cys Pro Arg Arg Tyr Lys Gln Ile Gly Thr Cys Gly Leu
             20                  25                  30
Pro Gly Thr Lys Cys Cys Lys Lys Pro
         35                  40
```

<210> SEQ ID NO 11
<211> LENGTH: 36
<212> TYPE: PRT
<213> ORGANISM: Pan troglodytes

<400> SEQUENCE: 11

```
Asp His Tyr Asn Cys Val Ser Ser Gly Gly Gln Cys Leu Tyr Ser Ala
  1               5                  10                  15
Cys Pro Ile Phe Thr Lys Ile Gln Gly Thr Cys Tyr Gly Gly Lys Ala
             20                  25                  30
Lys Cys Cys Lys
         35
```

<210> SEQ ID NO 12
<211> LENGTH: 42
<212> TYPE: PRT
<213> ORGANISM: Pan troglodytes

<400> SEQUENCE: 12

Gly Ile Ile Asn Thr Leu Gln Lys Tyr Tyr Cys Arg Val Arg Gly Gly
1               5                   10                  15

Arg Cys Ala Val Leu Thr Cys Leu Pro Lys Glu Glu Gln Ile Gly Lys
            20                  25                  30

Cys Ser Thr Arg Gly Arg Lys Cys Cys Arg
        35                  40

<210> SEQ ID NO 13
<211> LENGTH: 41
<212> TYPE: PRT
<213> ORGANISM: Bos taurus

<400> SEQUENCE: 13

Gly Val Gly Asn Pro Val Ser Cys Val Arg Asn Lys Gly Ile Cys Val
1               5                   10                  15

Pro Ile Arg Cys Pro Gly Ser Met Lys Gln Ile Gly Thr Cys Val Gly
            20                  25                  30

Arg Ala Val Lys Cys Cys Arg Lys Lys
        35                  40

<210> SEQ ID NO 14
<211> LENGTH: 41
<212> TYPE: PRT
<213> ORGANISM: Bos taurus

<400> SEQUENCE: 14

Gly Val Arg Asn Ser Gln Ser Cys Arg Arg Asn Lys Gly Ile Cys Val
1               5                   10                  15

Pro Ile Arg Cys Pro Gly Ser Met Arg Gln Ile Gly Thr Cys Leu Gly
            20                  25                  30

Ala Gln Val Lys Cys Cys Arg Arg Lys
        35                  40

<210> SEQ ID NO 15
<211> LENGTH: 41
<212> TYPE: PRT
<213> ORGANISM: Bos taurus

<400> SEQUENCE: 15

Gly Ile Ser Asn Pro Leu Ser Cys Arg Leu Asn Arg Gly Ile Cys Val
1               5                   10                  15

Pro Ile Arg Cys Pro Gly Asn Leu Arg Gln Ile Gly Thr Cys Phe Thr
            20                  25                  30

Pro Ser Val Lys Cys Cys Arg Trp Arg
        35                  40

<210> SEQ ID NO 16
<211> LENGTH: 36
<212> TYPE: PRT
<213> ORGANISM: Mus musculus

<400> SEQUENCE: 16

Gln Tyr Lys Cys Leu Gln His Gly Gly Phe Cys Leu Arg Ser Ser Cys
1               5                   10                  15

```
Pro Ser Asn Thr Lys Leu Gln Gly Thr Cys Lys Pro Asp Lys Pro Asn
            20                  25                  30

Cys Cys Lys Ser
        35

<210> SEQ ID NO 17
<211> LENGTH: 51
<212> TYPE: PRT
<213> ORGANISM: Mus musculus

<400> SEQUENCE: 17

Ala Val Gly Ser Leu Lys Ser Ile Gly Tyr Glu Ala Glu Leu Asp His
1               5                   10                  15

Cys His Thr Asn Gly Gly Tyr Cys Val Arg Ala Ile Cys Pro Pro Ser
            20                  25                  30

Ala Arg Arg Pro Gly Ser Cys Phe Pro Glu Lys Asn Pro Cys Cys Lys
        35                  40                  45

Tyr Met Lys
        50

<210> SEQ ID NO 18
<211> LENGTH: 41
<212> TYPE: PRT
<213> ORGANISM: Mus musculus

<400> SEQUENCE: 18

Lys Lys Ile Asn Asn Pro Val Ser Cys Leu Arg Lys Gly Gly Arg Cys
1               5                   10                  15

Trp Asn Arg Cys Ile Gly Asn Thr Arg Gln Ile Gly Ser Cys Gly Val
            20                  25                  30

Pro Phe Leu Lys Cys Cys Lys Arg Lys
        35                  40

<210> SEQ ID NO 19
<211> LENGTH: 41
<212> TYPE: PRT
<213> ORGANISM: Mus musculus

<400> SEQUENCE: 19

Gln Ile Ile Asn Asn Pro Ile Thr Cys Met Thr Asn Gly Ala Ile Cys
1               5                   10                  15

Trp Gly Pro Cys Pro Thr Ala Phe Arg Gln Ile Gly Asn Cys Gly His
            20                  25                  30

Phe Lys Val Arg Cys Cys Lys Ile Arg
        35                  40

<210> SEQ ID NO 20
<211> LENGTH: 41
<212> TYPE: PRT
<213> ORGANISM: Mus musculus

<400> SEQUENCE: 20

Gln Leu Ile Asn Ser Pro Val Thr Cys Met Ser Tyr Gly Gly Ser Cys
1               5                   10                  15

Gln Arg Ser Cys Asn Gly Gly Phe Arg Leu Gly Gly His Cys Gly His
            20                  25                  30

Pro Lys Ile Arg Cys Cys Arg Arg Lys
        35                  40
```

<210> SEQ ID NO 21
<211> LENGTH: 49
<212> TYPE: PRT
<213> ORGANISM: Mus musculus

<400> SEQUENCE: 21

Gln Asp Ile Asn Ser Lys Arg Ala Cys Tyr Arg Glu Gly Gly Glu Cys
1               5                   10                  15

Leu Gln Arg Cys Ile Gly Leu Phe His Lys Ile Gly Thr Cys Asn Phe
            20                  25                  30

Arg Phe Lys Cys Cys Lys Phe Gln Ile Pro Glu Lys Lys Thr Lys Ile
        35                  40                  45

Leu

<210> SEQ ID NO 22
<211> LENGTH: 38
<212> TYPE: PRT
<213> ORGANISM: Capra hircus

<400> SEQUENCE: 22

Ser Arg Arg Ser Cys His Arg Asn Lys Gly Val Cys Ala Leu Thr Arg
1               5                   10                  15

Cys Pro Arg Asn Met Arg Gln Ile Gly Thr Cys Phe Gly Pro Pro Val
            20                  25                  30

Lys Cys Cys Arg Lys Lys
        35

<210> SEQ ID NO 23
<211> LENGTH: 42
<212> TYPE: PRT
<213> ORGANISM: Capra hircus

<400> SEQUENCE: 23

Gln Gly Ile Ile Asn His Arg Ser Cys Tyr Arg Asn Lys Gly Val Cys
1               5                   10                  15

Ala Pro Ala Arg Cys Pro Arg Asn Met Arg Gln Ile Gly Thr Cys His
            20                  25                  30

Gly Pro Pro Val Lys Cys Cys Arg Lys Lys
        35                  40

<210> SEQ ID NO 24
<211> LENGTH: 42
<212> TYPE: PRT
<213> ORGANISM: Ovis aries

<400> SEQUENCE: 24

Gln Gly Val Arg Asn Arg Leu Ser Cys His Arg Asn Lys Gly Val Cys
1               5                   10                  15

Val Pro Ser Arg Cys Pro Arg His Met Arg Gln Ile Gly Thr Cys Arg
            20                  25                  30

Gly Pro Pro Val Lys Cys Cys Arg Lys Lys
        35                  40

<210> SEQ ID NO 25
<211> LENGTH: 42
<212> TYPE: PRT
<213> ORGANISM: Ovis orientalis aries

<400> SEQUENCE: 25

His Gly Val Thr Asp Ser Leu Ser Cys Arg Trp Lys Lys Gly Ile Cys
1               5                   10                  15

```
Val Leu Thr Arg Cys Pro Gly Thr Met Arg Gln Ile Gly Thr Cys Gly
            20                  25                  30

Gly Pro Pro Val Lys Cys Cys Arg Leu Lys
            35                  40

<210> SEQ ID NO 26
<211> LENGTH: 41
<212> TYPE: PRT
<213> ORGANISM: Sus scrofa

<400> SEQUENCE: 26

Asn Ile Gly Asn Ser Val Ser Cys Leu Arg Asn Lys Gly Val Cys Met
 1               5                  10                  15

Pro Gly Lys Cys Ala Pro Lys Met Lys Gln Ile Gly Thr Cys Gly Met
            20                  25                  30

Pro Gln Val Lys Cys Cys Lys Arg Lys
            35                  40
```

PEPTIDES HAVING ANTIMICROBIAL PROPERTIES AND COMPOSITIONS CONTAINING THEM, NOTABLY FOR THE PRESERVATION OF FOODSTUFFS

RELATED APPLICATION

This is a continuation of International Application No. PCT/FR2003/002041, with an international filing date of Jul. 1, 2003 (WO 2004/003006, published Jan. 8, 2004), which is based on French Patent Application No. 02/08207, filed Jul. 1, 2002.

FIELD OF THE INVENTION

This invention pertains to the field of the preservation of foodstuffs and the fight against microbial, bacterial and/or fungal infections in human, animals and plants. The invention pertains more particularly to peptides and compositions containing them for preventing and/or treating infections by pathogenic agents such as microbes, bacteria and fungi as well as for the preservation of foodstuffs.

BACKGROUND

It has been reported that the king penguin male, when on land to provide for the final part of incubation, is capable of retaining food in his stomach for two weeks (Gauthier-Clerc et al., 2000). The bird itself fasts and lives off of his body reserves.

To date, no similar situation is known of a higher vertebrate storing food for multiple weeks. The state of preservation of this food is remarkable since its mass and calorific value are not modified (Gauthier-Clerc et al., 2002). These observations on the state of preservation of the food strongly suggest a control of the bacterial flora present in the stomach contents. Such control of the bacterial flora would make it possible to reduce degradation of stored food. This control could be implemented via the production of substances with antimicrobial activity.

In fact, the literature reports the existence of substances with antimicrobial activity in the gastrointestinal tract of vertebrates. A major part of these substances are of a peptide nature, notably magainins, brevinins and buforins in amphibians (Moore et al., 1991; Minn et al., 1998; Wang et al., 1998), lactoferricins and defensins ($\alpha$, $\beta$) in mammals, including humans (Jones and Bevins, 1992; Zhao et al., 1999; O'Neil et al., 2000). In birds, defensins have been found in other parts of the digestive tract notably the tongue, esophagus and intestine (Zhao et al., 2001). Numerous antimicrobial peptides are, moreover, present in the surface epithelia (for review, see Schröder, 1999).

SUMMARY OF THE INVENTION

This invention relates to a peptide including one or more intramolecular bonds corresponding to formula (I):

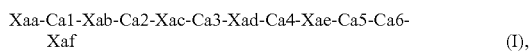

$$\text{Xaa-Ca1-Xab-Ca2-Xac-Ca3-Xad-Ca4-Xae-Ca5-Ca6-Xaf} \quad (I),$$

wherein Xaa represents an —$NH_2$ group, a peptide residue of 1 to 16 amino acids or -Xaa1-Xaa2- in which Xaa1 represents an —$NH_2$ group or a peptide residue of 1 to 13 amino acids and Xaa2 represents a peptide residue of 3 amino acids selected from the group consisting of hydrophobic amino acids and apolar amino acids; Xab represents a peptide residue of 1 to 6 amino acids or -Xab1-Xab2-Xab3-Xab4-Xab5- in which Xab1, Xab2, Xab4 and Xab5, when present and which can be identical or different, are selected from the group consisting of basic amino acids, negatively charged polar amino acids, small noncharged polar amino acids, large noncharged polar amino acids and hydrophobic or apolar amino acids, and Xab3 represents -Xab3.1-Xab3.2- in which those of the Xab3.1 and Xab.3,2, when present and which can be identical or different, are selected from the group consisting of basic amino acids, negatively charged polar amino acids, small noncharged polar amino acids, large noncharged polar amino acids and hydrophobic or apolar amino acids; Xac represents a peptide residue comprising 1 to 4 amino acids or -Xac1-Xac2-Xac3-Xac4- in which those of the Xac1, Xac2, Xac3 and Xac4, when present and which can be identical or different, are selected from the group consisting of basic amino acids, small noncharged polar amino acids, hydrophobic or apolar amino acids and large noncharged polar amino acids; Xad represents a peptide residue comprising 1 to 9 amino acids or -Xad1-Xad2-Xad3-Xad4-Xad5-Xad6-Xad7-Xad8-Xad9- in which those of Xad1, Xad2, Xad3, Xad4, Xad5, Xad6, Xad7, Xad8 and Xad9, when present and which can be identical or different, are selected from the group consisting of basic amino acids, small noncharged polar amino acids, hydrophobic or apolar amino acids, large noncharged polar amino acids and negatively charged polar amino acids; Xae represents a peptide residue comprising 1 to 6 amino acids or -Xae1-Xae2-Xae3-Xae4-Xae5- in which those of Xae1, Xae2, Xae3, Xae4, Xae5, when present and which can be identical or different, are selected from the group consisting of basic amino acids, small noncharged polar amino acids, hydrophobic or apolar amino acids, large noncharged polar amino acids and negatively charged polar amino acids; Xaf represents —OH, —$CONH_2$, a peptide residue of 1 to 14 amino acids or -Xaf1-Xaf2-Xaf3-Xaf4 in which those of the Xaf1, Xaf2, Xaf3 and Xaf4, when present and which can be identical or different, are selected from the group consisting of basic amino acids, small noncharged polar amino acids, hydrophobic or apolar amino acids, large noncharged polar amino acids and negatively charged polar amino acids; and Ca1, Ca2, Ca3, Ca4, Ca5 and Ca6, which can be identical or different, represent amino acids at least one of which is bonded to any one of Ca1, Ca2, Ca3, Ca4, Ca5.

This invention also relates to a pharmaceutical composition including a therapeutically effective amount of an active agent including at least one peptide and a carrier.

This invention further relates to a food processing composition including an effective amount of an active agent including at least the peptide and a carrier.

This invention still further relates to an agricultural composition including an effective amount of the active agent including at least the peptide and the carrier.

This invention yet again relates to a polynucleotide that codes for the peptide.

This invention also again relates to a nucleic acid molecule as a vector including at least the polynucleotide.

This invention further again relates to a host including an animal cell, plant cell or a prokaryote and the nucleic acid molecule.

This invention further yet relates to a method of treating bacterial and/or fungal infections in mammals including administering a therapeutically effective amount of the pharmaceutical composition to the mammal.

This invention further still relates to a method of preventing bacterial and/or fungal infections in mammals including administering a therapeutically effective amount of the composition to the mammal.

This invention again further relates to a method of treating bacterial and/or fungal infections in plants including administering a therapeutically effective amount of the pharmaceutical composition to a plant.

Finally, this invention relates to a method of preventing bacterial and/or fungal infections in plants including administering a therapeutically effective amount of the pharmaceutical composition to the plant.

BRIEF DESCRIPTION OF THE DRAWINGS

Other advantages and characteristics of the invention will become apparent from the examples below pertaining to the demonstration, isolation and characterization of antimicrobial peptides from samples of the stomach contents of male king penguins as well as the synthetic form of *spheniscin*-2, its spectrum of antimicrobial activity and the study of the effect of pH on its functionality. These examples will make reference to the attached figures and tables in which:

FIG. 8 is a table showing the β-defensins implicated in the epithelial immune response in vertebrates. The β-defensins shown are: Spheniscin-1 (*Aptenodytes patagonicus*) (SEQ ID NO: 1), Spheniscin-2 (*A. patagonicus*) (SEQ ID NO: 2), Gallinacin-3 (*gallus callus*) (SEQ ID NO: 3), Gallopavin-1 (*Meleagris gallopavo*) (SEQ ID NO: 4), HBD 1 (*Homo sapiens*) (SEQ ID NO: 5), HBD 2 (*H. sapiens*) (SEQ ID NO: 6), HBD 3 (*H. sapiens*) (SEQ ID NO: 7), HBD 4 (*H sapiens*) (SEQ ID NO: 8), rhBD 1 (*Macaca mulatta*) (SEQ ID NO: 9), rhBD 2 (*M. mulatta*) (SEQ ID NO:10), CBD 1 (*Pan troglodytes*) (SEQ ID NO: 11), CBD 3 (*P. troglodytes*) (SEQ ID NO: 12), TAP (*Bos taurus*) (SEQ ID NO: 13), LAP (*B. taurus*) (SEQ ID NO: 14), EBD (*B. taurus*) (SEQ ID NO: 15), MBD 1 (*M. musculus*) (SEQ ID NO: 16), MBD 2 (*M. musculus*) (SEQ ID NO: 17), MBD 3 (*M. musculus*) (SEQ ID NO: 18), MBD 4 (*M. musculus*) (SEQ ID NO: 19), MBD 6 (*M. musculus*) (SEQ ID NO: 20), MBD 7 (*M. musculus*) (SEQ ID NO: 21), GBD 1 (*Capra hircus*) (SEQ ID NO: 22), GBD 2 (*C. hircus*) (SEQ ID NO: 23), SBD 1 (*Ovis. aries*) (SEQ ID NO: 24), SBD 2 (*O. orientalis aries*) (SEQ ID NO: 25) and PBD 1 (*Sus scrofa*) (SEQ ID NO: 26). L =tongue; T =trachea; MB =buccal mucosa; GS =salivary glands; P =skin; MP =pulmonary mucosa; GI =gastrointestinal tract; E =stomach; I =intestine; O =esophagus; TG =genital tract. References: (1) Zhao et al., 2001; (2) Harder et al., 1997; (3) Hiratsuka et al., 1998; (4) Mathews et al., 1999; (5) Harder et al., 2001; (6) Garcí a et al., 2001a; (7) Garcí a et al., 2001b; (8) Bals et al., 2001; (9) Duits et al., 2000; (10) Duits et al., site AMSDb; (11) Diamond et al., 1993; (12) Schonwetter et al., 1995; (13) Tarver et al., 1998; (14) Bals et al., 1998; (15) Huttner et al., 1997; (16) Morrison et al., 1999; (17) Bals et al., 1999; (18) Jia et al., 2000; (19) Yamaguchi et al., 2001; (20) Conejo-Garcia et al., site AMSDb; (21) Zhao et al., 1999; (22) Huttner et al., 1998; (23) Zhang et al., 1998.

(FIG. 9A) Control growth: the aspergillar heads terminated by the spores are clearly visible (X 400). (FIG. 9B) Incubation with 6 μM of *spheniscin*-2 leads to the disappearance of the *aspergillar* heads. The effect of *spheniscin*-2 on *A. fumigatus* is consequently not of the direct fungicidal type on the spores but is manifested by a halt of growth by inhibition of the reproduction of the fungus because there is no longer formation of *aspergillar* heads, structures implicated in the reproduction/proliferation process of this fungus.

DETAILED DESCRIPTION

Figure 1:
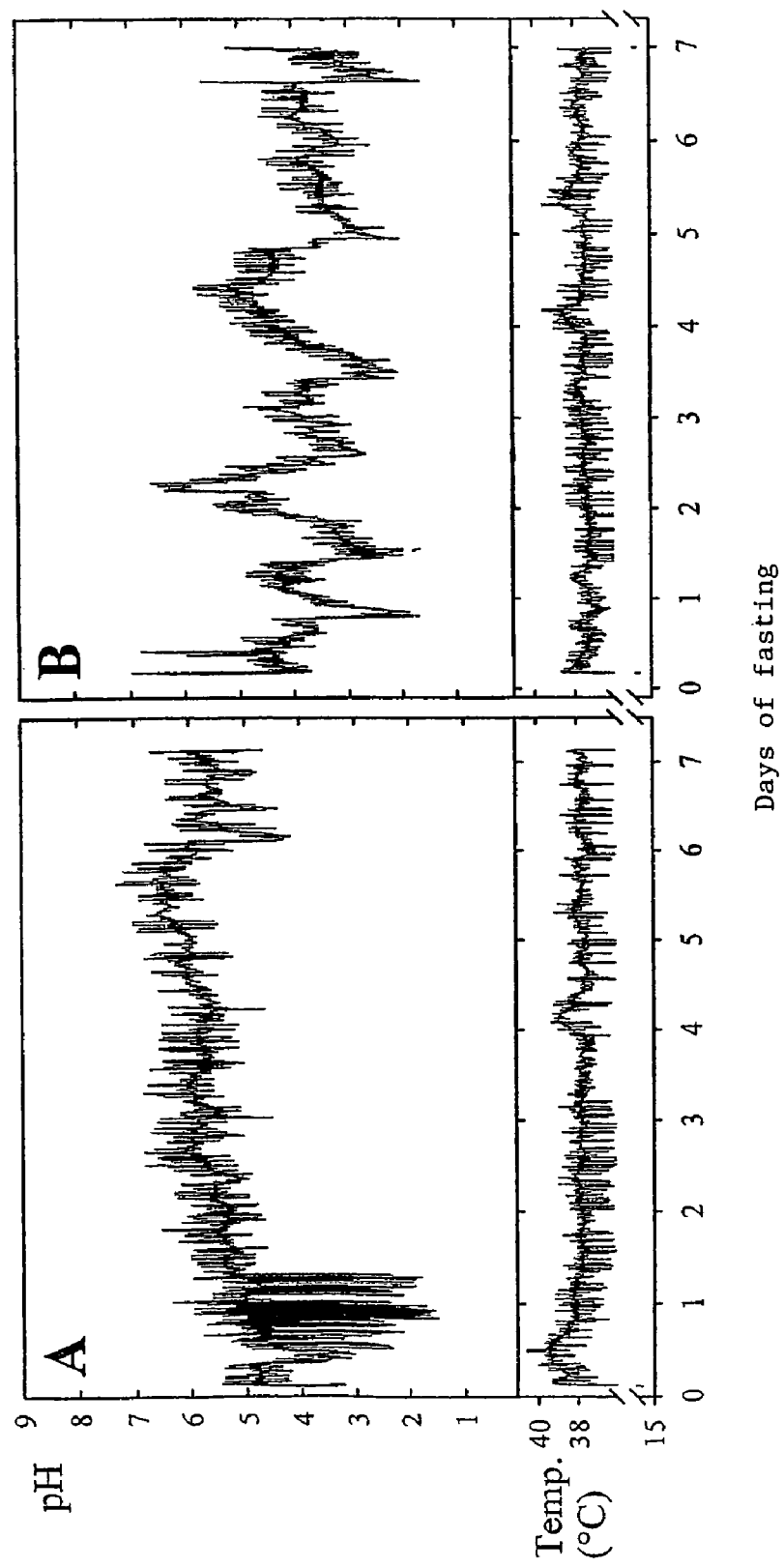
FIG. 1 is a graph showing the evolution of the gastric pH and the stomach temperature in two male king penguins during the first week of their incubation fast. The stomach content was preserved in one case (A) and digested in the other case (B).

We have now discovered the presence of antimicrobial peptides in the stomach content of king penguins and the implication of these peptides with antimicrobial activity in the phenomenon of preservation of the alimentary bolus during incubation fasting in the king penguin male. We thereby discovered new peptides which are designated below as "*spheniscins*" after the family of the *Spheniscidae* to which the king penguin belongs.

The invention thus provides a purified peptide from the stomach contents of king penguins or an analogue of that peptide provided that the analogue has antibacterial activity in one of the tests described herein. An analogue has a sequence modified by addition, suppression or replacement of at least one amino acid residue of the sequence of the peptide.

The invention pertains most particularly to a peptide comprising one or more intramolecular bonds corresponding to the sequence of formula (I) below:

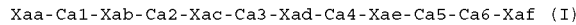

Xaa-Ca1-Xab-Ca2-Xac-Ca3-Xad-Ca4-Xae-Ca5-Ca6-Xaf   (I)

in which:

Xaa represents an —NH$_2$ group or a peptide residue of 1 to 16 amino acids, preferably 4 amino acids; Xaa advantageously corresponds to the following formula: —Xaa1-Xaa2 in which Xaa1 represents an —NH$_2$ group or a peptide residue of 1 to 13 amino acids and Xaa2 represents a peptide residue of 3 amino acids selected from among the hydrophobic or apolar amino acids;

—Xab represents a peptide residue of 1 to 6 amino acids, preferably 6 amino acids; Xab advantageously corresponds to the following formula: —Xab1-Xab2-Xab3-Xab4-Xab5 - in which those of the Xab1, Xab2, Xab4 and Xab5, which can be identical or different, are selected from among the group comprising the basic amino acids, the negatively charged polar amino acids, the small noncharged polar amino acids, the large noncharged polar amino acids and the hydrophobic or apolar amino acids, and Xab3 represents a peptide residue corresponding to the following formula: —Xab3.1-Xab3.2- in which those of the Xab3.1 and Xab.3, which can be identical or different, are selected from among the group comprising the basic amino acids, the negatively charged polar amino acids, the small noncharged polar amino acids, the large noncharged polar amino acids and the hydrophobic or apolar amino acids;

Xac represents a peptide residue comprising 1 to 4 amino acids, preferably 4 amino acids; Xac advantageously corresponds to the following formula: —Xac1-Xac2-Xac3-Xac4- in which those of the Xac 1, Xac2, Xac3 and Xac4, which can be identical or different, are selected from among the group comprising the basic amino acids, the small noncharged polar amino acids, the hydrophobic or apolar amino acids and the large noncharged polar amino acids;

Xad represents a peptide residue comprising 1 to 9 amino acids, preferably 9 amino acids; Xad advantageously responds to the following sequence: —Xad1-Xad2-Xad3-Xad4-Xad5-Xad6 -Xad 7-Xad8-Xad9 in which those of the Xad1, Xad2, Xad3, Xad4, Xad5, Xad6, Xad7, Xad8 and Xad9, which can be identical or different, are selected from among the group comprising the basic amino acids, the small noncharged polar amino acids, the hydrophobic or apolar amino acids, the large noncharged polar amino acids and the negatively charged polar amino acids;

Xae represents a peptide residue comprising 1 to 6 amino acids, preferably 5 amino acids; Xae advantageously corresponds to the following sequence: —Xae1-Xae2-Xae3-Xae4-Xae5- in which those of the Xae 1, Xae2, Xae3, Xae4, Xae5, which can be identical or different, are selected from among the group comprising the basic amino acids, the small noncharged polar amino acids, the hydrophobic or apolar amino acids, the large noncharged polar amino acids and the negatively charged polar amino acids;

Xaf represents an —OH or —CONH2 group or a peptide residue of 1 to 14 amino acids, preferably 4 amino acids; Xaf advantageously corresponds to the following sequence: —Xaf1-Xaf2 -Xaf3-Xaf4 - in which those of the Xaf1, Xaf2, Xat3 and Xaf4, which can be identical or different, are selected from among the group comprising the basic amino acids, the small noncharged polar amino acids, the hydrophobic or apolar amino acids, the large noncharged polar amino acids and the negatively charged polar amino acids;

Ca1, Ca2, Ca3, Ca4, Ca5 and Ca6, which can be identical or different, represent amino acids at least one of which is bonded to any one of the others Cal, Ca2, Ca3, Ca4, Ca5 and Ca6; Cal, Ca2, Ca3, Ca4, Ca5 and Ca6 are advantageously sulfur-containing amino acids of the cysteine type, preferably cysteines.

The invention pertains most particularly to the peptides of formula (I) having one or more of the following characteristics:

Xaa1 is an amino acid selected from among the small noncharged polar amino acids, preferably serine;

Xaa2 is Phe-Gly-Leu;

Ca1 and Ca5 are linked by covalence;

Xab1 is selected from among the group comprising the basic amino acids, the hydrophobic or apolar amino acids and the large noncharged polar amino acids; Xab1 preferably is a basic amino acid, most preferably arginine (Arg);

Xab2 is selected from among the group comprising the hydrophobic or apolar amino acids, the small noncharged polar amino acids, the basic amino acids and the large noncharged polar amino acids; Xab2 is preferably a hydrophobic or apolar amino acid, most preferably leucine (Leu);

Xab3.2 is selected from among the group containing the basic amino acids, the small noncharged polar amino acids and the hydrophobic or apolar amino acids, most preferably arginine (Arg);

Xab4 is selected from among the group comprising the hydrophobic or apolar amino acids, most preferably Xab4 is glycine (Gly);

Xab5 is selected from among the group comprising the hydrophobic or apolar amino acids, the large noncharged polar amino acids, the basic amino acids, the negatively charged polar amino acids and the small noncharged polar amino acids; Xab5 is preferably a hydrophobic or apolar amino acid, most preferably phenylalanine (Phe);

Ca2 and Ca4 are linked by covalence;

Xac1 is selected from among the group comprising the basic amino acids, the hydrophobic or apolar amino acids and the large noncharged polar amino acids; Xac1 is preferably a hydrophobic or apolar amino acid, most preferably alanine (Ala);

Xac2 is selected from among the group comprising the basic amino acids, the hydrophobic or apolar amino acids and the large noncharged polar amino acids; Xac2 is preferably a basic amino acid, most preferably arginine (Arg) or histidine (His);

Xac3 is selected from among the group comprising the basic amino acids, the hydrophobic or apolar amino acids, the small noncharged polar amino acids and the large noncharged polar amino acids; Xax3 is preferably a hydrophobic or apolar amino acid, most preferably glycine (Gly);

Xac4 is selected from among the group comprising the basic amino acids, the hydrophobic or apolar amino acids and the small noncharged polar amino acids; Xac4 is preferably a basic amino acid, most preferably arginine (Arg);

Ca3 and Ca6 are linked by covalence;

Xad1 is selected from among the group comprising the basic amino acids, the hydrophobic or apolar amino acids and the large noncharged polar amino acids; Xad1 is preferably a basic amino acid, most preferably arginine (Arg);

Xad2 is selected from among the group comprising the hydrophobic or apolar amino acids, the small noncharged polar amino acids and the basic amino acids; Xad2 is preferably a hydrophobic or apolar amino acid, most preferably phenylalanine (Phe);

Xad3 is selected from among the group comprising the hydrophobic or apolar amino acids, the small noncharged polar amino acids, the basic amino acids and the large noncharged polar amino acids; Xad3 is preferably a hydrophobic or apolar amino acid, preferably proline or hydroxyproline, most preferably proline (Pro);

Xad4 is selected from among the group comprising the hydrophobic or apolar amino acids, the small noncharged polar amino acids, the basic amino acids, the large noncharged polar amino acids and the negatively charged polar amino acids; Xad4 is preferably a small noncharged polar amino acid, most preferably serine (Ser);

Xad5 is selected from among the group comprising the hydrophobic or apolar amino acids, the basic amino acids and the negatively charged polar amino acids; Xad5 is preferably a hydrophobic or apolar amino acid, most preferably isoleucine (Ile);

Xad6 is selected from among the group comprising the hydrophobic or apolar amino acids, the basic amino acids and the large noncharged polar amino acids; Xad6 is preferably a hydrophobic or apolar amino acid, preferably proline or hydroxyproline, most preferably proline (Pro);

Xad7 is selected from among the group comprising the hydrophobic or apolar amino acids and the large noncharged polar amino acids; Xad7 is preferably a hydrophobic or apolar amino acid, most preferably isoleucine (Ile);

Xad8 is selected from among the group comprising the hydrophobic or apolar amino acids; Xad8 is preferably glycine (Gly);

Xad9 is selected from among the group comprising the basic amino acids, the large noncharged polar amino acids and the small noncharged polar amino acids; Xad9 is preferably a basic amino acid, most preferably arginine (Arg);

Xae1 is selected from among the group comprising the basic amino acids, the hydrophobic or apolar amino acids, the large noncharged polar amino acids and the small noncharged polar amino acids; Xae1 is preferably a small noncharged polar amino acid, most preferably serine (Ser);

Xae2 is selected from among the group comprising the basic amino acids, the hydrophobic or apolar amino acids, the large noncharged polar amino acids and the small noncharged polar amino acids; Xae2 is preferably a basic amino acid, most preferably arginine (Arg);

Xae3 is selected from among the group comprising the basic amino acids, the hydrophobic or apolar amino acids, the large noncharged polar amino acids, the small noncharged polar amino acids and the negatively charged polar amino acids; Xae3 is preferably a hydrophobic or apolar amino acid, most preferably phenylalanine (Phe);

Xae4 is selected from among the group comprising the basic amino acids, the hydrophobic or apolar amino acids, the large noncharged polar amino acids and the small noncharged polar amino acids; Xae4 is preferably a hydrophobic or apolar amino acid, most preferably valine (Val);

Xae5 is selected from among the group comprising the basic amino acids, the hydrophobic or apolar amino acids, the large noncharged polar amino acids and the small noncharged polar amino acids; Xae5 is preferably a large noncharged polar amino acid, most preferably glutamine (Gln);

Xaf1 is selected from among the group comprising the basic amino acids and the hydrophobic or apolar amino acids; Xae5 is preferably a basic amino acid, most preferably arginine (Arg);

Xaf2 is selected from among the group comprising the basic amino acids, the hydrophobic or apolar amino acids and the small noncharged polar amino acids; Xaf2 is preferably a basic amino acid, most preferably arginine (Arg);

Xaf3 is selected from among the group comprising the basic amino acids, the hydrophobic or apolar amino acids and the large noncharged polar amino acids; Xaf3 is preferably a hydrophobic or apolar amino acid, most preferably valine (Val);

Xaf4 is selected from among the group comprising the basic amino acids and the hydrophobic or apolar amino acids; Xaf4 is preferably a hydrophobic or apolar amino acid, most preferably tryptophan (Trp).

The particular meanings of the following terms are:

basic amino acids: lysine (Lys), arginine (Arg), histidine (His) or homoarginine;

negatively charged polar amino acids: aspartic acid (Asp) or aspartate or glutamic acid (Glu) or glutamate;

small noncharged polar amino acids: serine (Ser) or threonine (Thr);

large noncharged polar amino acids: asparagine (Asn), glutamine (Gln) or methionine (Met);

hydrophobic or apolar amino acids: isoleucine (Ile), leucine (Leu), phenylalanine (Phe), tryptophan (Trp), tyrosine (Tyr), valine (Val), alanine (Ala), glycine (Gly), proline (Pro) or hydroxyproline.

The invention pertains specifically to a peptide of formula (I) having three intramolecular bonds, more particularly, three disulfide bridges and, among these, the invention pertains to a peptide of formula (II) below:

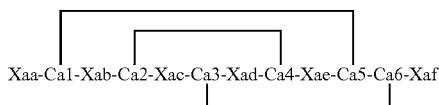
(II)

in which Xaa, Ca1, Xab, Ca2, Xac, Ca3, Xad, Ca4, Xae, Ca5, Ca6 and Xaf have the same meanings as in formula (I).

The invention pertains particularly to the peptides of formula (II) in which:

```
Xac is: Xac1-His-Xac3
or

Xac1-Arg-Xac3;

Xad is: Xad1-Pro-Xad3;

Xae is: Xae1-Gln-Xae3;

Xaf is: Xaf1-Val-Xaf3
``` in which Xac, Xac1, Xac3, Xad, Xad1, Xad3, Xae, Xae1, Xae3, Xaf, Xaf1 and Xaf3 have the same meanings as in formula (I).

The following can be cited as particular non-limiting examples of peptides of formula (I) or (II):

*spheniscin*-1, the primary sequence of which is the following:

```
                            (SEQ ID NO:1)
SFGLCRLRRGFCAHGRCRFPSIPIGRCSRFVQCCRRVW,
```

*spheniscin*-2, the primary sequence of which is the following:

```
                            (SEQ ID NO:2)
SFGLCRLRRGFCARGRCRFPSIPIGRCSRFVQCCRRVW.
```

The amino acids are generally represented by their single letter code but they can also be represented by their three-letter code according to the nomenclature below:

| A | Ala | Alanine |
|---|-----|---------|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The peptides of the invention can have at the level of certain amino acids natural or chemical post-translational modifications, e.g., the $NH_2$-terminal residue can have, e.g., an acylation, or the C-terminal residue can have a natural or chemical post-translational modification, e.g., an amidation, an oxidation or an esterification. The invention thus also pertains to derivatives of peptides of formulas (I) or (II) such as those in which one or more amino acids are amino acids of D conformation. The invention also relates to retro-peptides and retro-inverso-peptides, provided that they preserve antimicrobial activity.

The invention also provides a method of using the peptides in the food-processing field for protecting foodstuffs against microbes (bacteria and fungi). The invention further provides a method of using the peptides in humans, animals or plants to prevent and/or treat microbial, bacterial and/or fungal infection.

The invention thus pertains to a pharmaceutical, agricultural or food processing composition comprising as an active agent at least one peptide as defined above, advantageously combined in the composition with one or more pharmaceutically acceptable vehicles, diluents, excipients, carriers or the like.

The vehicles, diluents, carriers and excipients are selected as a function of the type of application of the composition, e.g., whether pharmaceutical, agricultural or food processing.

Thus, the invention also provides a peptide as defined above for a pharmaceutical, agricultural or food-processing preparation that is antibacterial and/or antifungal. The compositions of the invention may be used with both preventive and curative intent.

For use relative to the preservation of foodstuffs, the peptides of the invention and the compositions containing them can be made available in powder or granulate form. They can be fixed on the supports containing the foodstuffs or be incorporated directly in the foodstuffs notably in the form of microorganisms, such as yeasts, producing the peptides.

The administration of the pharmaceutical composition according to the invention can be implemented by any of the modes of administration accepted for therapeutic, agricultural or food-processing agents. For the pharmaceutical composition in humans or animals, systemic, topical or central administration can be cited. Oral administration can be implemented by means of tablets, gel capsules, soft capsules, including delayed or extended release formulations, pills, powders, granules, elixirs, tinctures, suspensions, syrups, emulsions and the like. Parenteral administration of antibacterial and/or antifungal compounds is generally performed by intramuscular or intravenous injection by perfusion. Injectable compositions can be prepared in conventional forms, either in suspension or liquid solution or in a solid form suitable for as needed dissolution in a suitable liquid, including formulations with delayed or prolonged release as well as the incorporation of peptides in biodegradable microparticles of lipidic formulation such as liposomes. Other conventional topical preparations include creams, unguents, lotions, gels, aerosol sprays and the like.

Use of the peptides with essentially preventive intent comprises applying the peptides to hygiene products, bandages and animal litter.

As a function of the mode of administration, the compounds can be in solid, semisolid or liquid form. For solid compositions such as tablets, pills, powders or granules in the free state or incorporated in gel capsules or biodegradable microparticles of lipidic formulation, such as liposomes, the active agent can be combined with diluents, lubricants, binders, absorbents, colorants, flavoring agents and sweeteners.

The compositions according to the invention can also contain other substances having therapeutic properties.

The peptides of the invention can be administered in the form of a single daily dose or the total daily dosage can be administered in two, three or four doses per day.

The invention includes not only the peptides described above but also the use of the polynucleotide sequences coding these peptides for transforming hosts, and notably animal or plant cells or prokaryotes. These sequences are used in accordance with the genetic engineering techniques described in the literature. The invention consequently also provides a polynucleotide coding a peptide described above, a nucleic acid molecule, DNA or RNA, as a vector, comprising the polynucleotide, and a host, e.g., an animal or plant cell or prokaryote comprising the nucleic acid molecule as well as the compositions—notably pharmaceutical compositions—containing them.

The invention also pertains to agricultural applications of the previously described peptides to make plants resistant to phytopathogenic bacteria and fungi and thereby reduce the use of chemical pesticides that are toxic for the environment. The direct application on the plant of an effective amount of antibacterial and/or antifungal peptides or of a composition containing them represents a first form of implementation of the agricultural application.

A second form of implementation of this application is based on transgenic techniques comprising incorporating in a stable manner in the DNA of a plant cell a polynucleotide sequence coding for one or more of the above peptides. The plant cells transformed in this manner enable regeneration of a plant transmitting the character of resistance to bacterial and/or fungal infections to its descendents. As examples of plants, the following can be cited: rice, corn, rape, beets, wheat, tobacco, tomatoes, potatoes and the like.

EXAMPLE 1

Demonstration of Antimicrobial Peptides in the Stomach Contents of King Penguins During Incubation Fasting Like most pelagic birds, king penguins feed themselves solely in the sea. They alternate periods at sea where they eat with fasting periods on land for reproduction and molting. The duration of the alimentary voyages at sea is, however, quite variable both in terms of duration and distance traveled due to variability both in the distance at which their prey is to be found, but also the availability of this prey within the zone of alimentary prospecting. The result is that the duration of these alimentary voyages can sometimes be doubled (Bost et al., 1997).

During the reproduction period, a male-female pair take turns providing for the incubation of the single egg (54 days), with the male normally providing for the final incubation period. Given the variability of the duration of the voyages at sea, there exists some uncertainty regarding the sex of the bird who will be on the egg at the moment of hatching. In the majority of cases, the female returns in time for hatching, but her return can be delayed by up to nine days (Gauthier-Clerc et al., 2000) whereas the endogenous reserves of the newborn chick can only provide for two or three days of self-sufficiency.

The male king penguin has developed a remarkable adaptation to ensure the survival of the chick in the case that the female is delayed. It has been confirmed that the male king penguin is capable while on land of providing for the last part of incubation to retain the food in his stomach for more than two weeks (Gauthier-Clerc et al., 2000). The male itself fasts and lives on his body reserves. The state of preservation of this food is remarkable since neither its mass nor its calorific value changes (Gauthier-Clerc et al., 2002).

Figure 2:
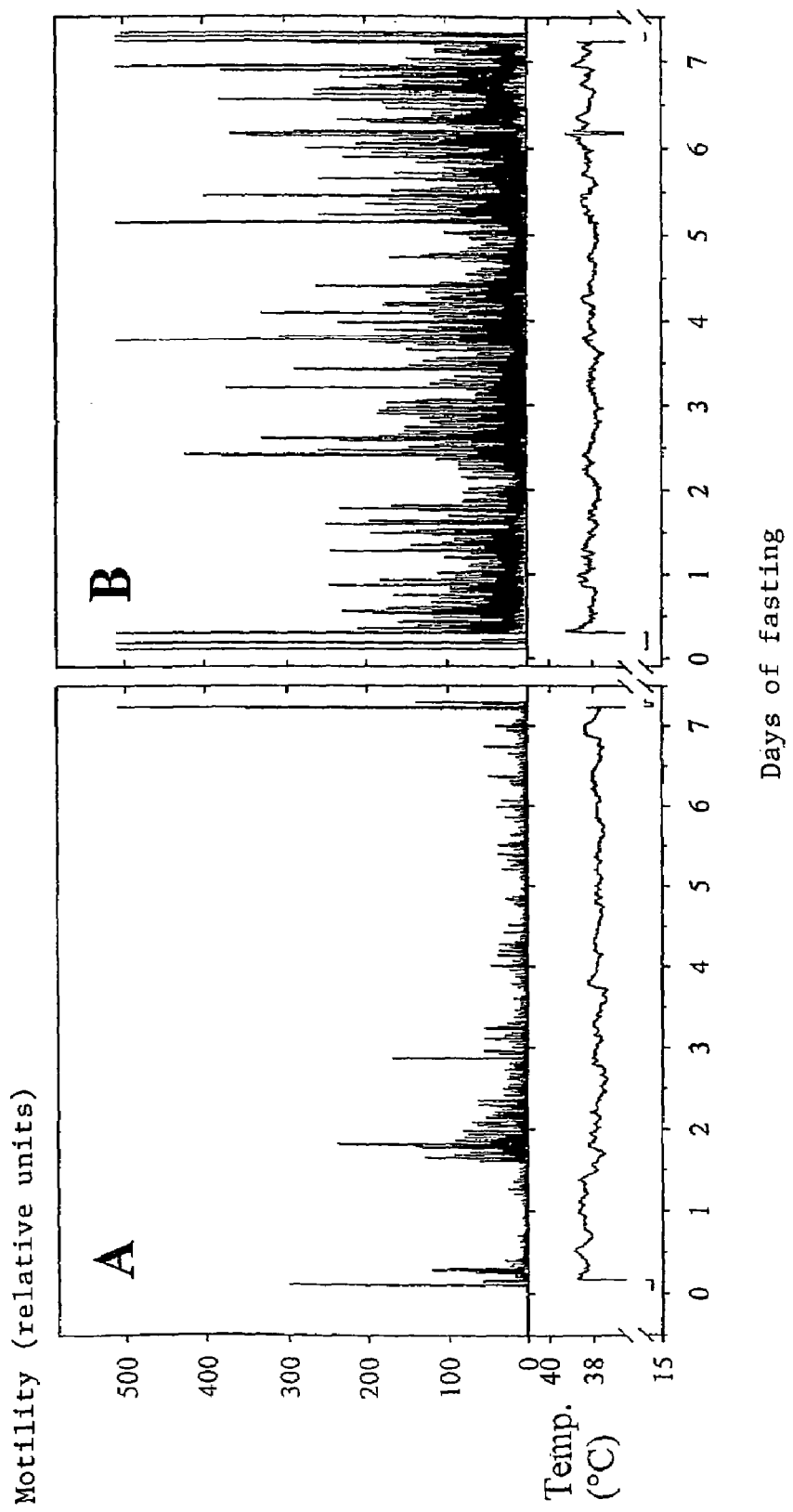
FIG. 2 is a graph showing the evolution of the gastric motility and the stomach temperature in two male king penguins during the first week of their incubation fast. The stomach content was preserved in one case (A) and digested in the other case (B).

During the preservation of this food, the stomach temperature is maintained at a high value, an average of 38° C., and the gastric pH remains between 5 and 6 (FIG. 1). The gastric motility is very greatly diminished in the case of preservation of the food compared to that which is seen in a bird that digests its stomach content during the incubation period (FIG. 2). Although these different parameters are favorable for the degradation of the food by the bacteria present in the stomach content, the qualitative and quantitative analysis of this food has shown that this is not the case at all.

A bacteriological study showed that there is a very high proportion of viable bacteria in the stomach contents of penguins which are effectively preserved during the fast, but they apparently are unable to develop. These bacteria in fact have the morphological characteristics of bacteria placed under conditions of environmental stress. The bacteria that can be cultured are principally the environmental bacteria such as the *Corynebacterium, Moraxella, Staphylococcus, Micrococcus* and *Streptococcus* spp. as well as bacteria that would seem to stem from the penguins' prey such as *Clostridium* spp. In contrast, multiple bacteria of the *Pseudomonas* and *Vibrio* spp. type present in the marine environment (MacCormack & Fraile, 1990) were not detected. Similarly, no enteric bacteria were demonstrated even though such bacteria have been observed in king penguins (Soucek and Mushin, 1970). Thus, the results of the analysis of the bacterial flora also are indicative of a protection of the stored food against degradation by bacteria. A control of the bacterial flora by antimicrobial substances produced by the birds could explain this preservation.

The presence of antimicrobial peptides was investigated in the stomach contents of king penguins during incubation fasting. There was thus performed:

an individual monitoring during fasting of the antimicrobial peptides present in the stomach contents. Multiple samples were collected for the same individual during fasting.

a comparison between two groups of birds depending on whether they preserved ("preservation" group) or digested ("digestion" group) their stomach contents during fasting (see example 2.1 for the detailed protocol).

Four strains of test microorganisms were selected for screening for the presence of antimicrobial peptides in the stomach content extracts: *Micrococcus luteus* (Gram positive), *Escherichia coli* SBS 363 (Gram negative), *Neurospora crassa* (filamentous fungus) and the yeast *Candida albicans*. These strains were selected because of their high sensitivity to antimicrobial peptides (see examples 2.2, 2.3 and 2.4 for the details of the protocol). We shall restrict our description to the activities directed against the bacterial strains *E. coli, M. luteus* and *N. crassa*.

Three major results emerge:

there exist molecules with antimicrobial activity in the stomach content samples from the male king penguins.

these antimicrobial activities are expressed differently in the individuals of the "preservation" group compared to the individuals of the "digestion" group. These differences are at both the quantitative and the qualitative levels.

Figure 3:
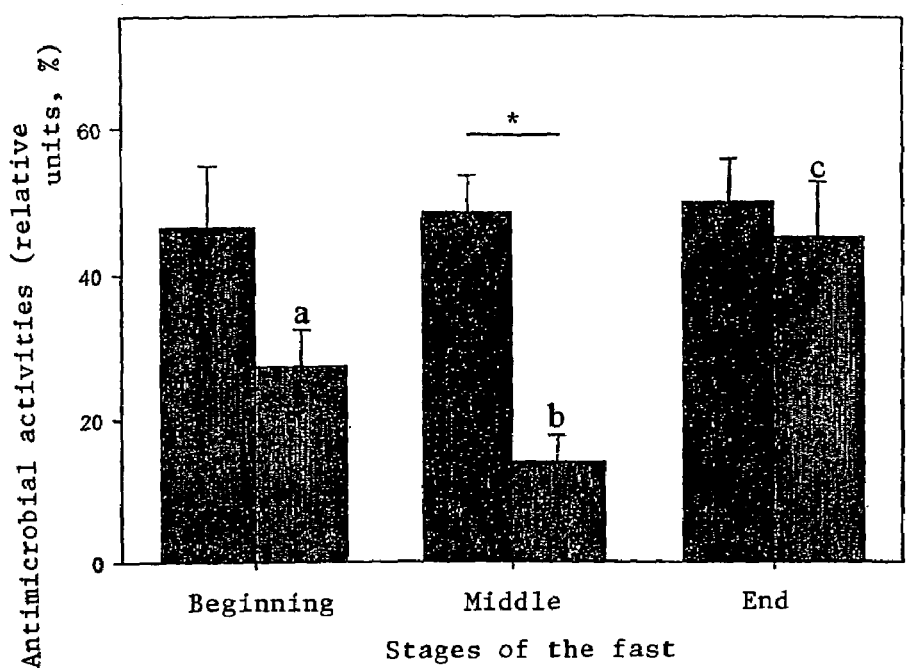
FIG. 3 is a graph showing the evolution of the antimicrobial activities in the stomach content of fasting king penguins incubating their eggs. The antimicrobial activities were testing by depositing fractions stemming from a first purification by chromatography of the cationic peptides. Three strains of microorganisms, representatives of Gram-negative bacteria (*Escherichia coli*), Gram-positive bacteria (*Micrococcus luteus*) and filamentous fungi (*Neurospora crassa*) were used. The antimicrobial activity corresponds to a diminishment in or absence of growth of the microorganisms for a tested fraction. The percentage indicated for the antimicrobial activities corresponds to the proportion of fraction having these activities. Two groups of king penguins were constituted depending on whether the birds preserved (dark histograms at left) or digested (lighter histograms at right) their stomach contents during the fast. Letters: difference over the course of the fast for the same group; P<0.05. Star: differences for the same stage of fasting between the groups; P<0.05.
Figure 4:
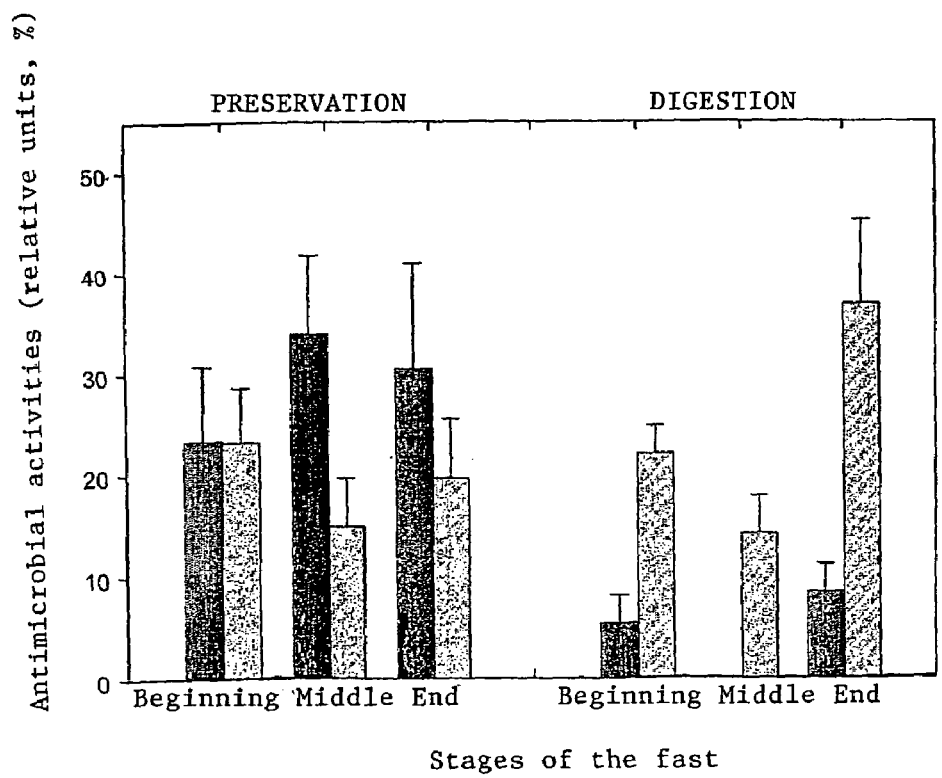
FIG. 4 is a graph showing the evolution of the total (solid histograms) or partial (hatched histograms) antimicrobial activities in the fasting male king penguins incubating their eggs. The antimicrobial activities were tested by depositing fractions stemming from a first purification by chromatography of the cationic peptides. Three strains of microorganisms, representatives of Gram-negative bacteria (*Escherichia coli*), Gram-positive bacteria (*Micrococcus luteus*) and filamentous fungi (*Neurospora crassa*) were used. The antimicrobial activity was characterized as total if there was no growth of microorganisms for a tested fraction. If the growth was only slowed down, the inhibition was partial. The percentage indicated for the antimicrobial activities, whether total or partial, corresponds to the proportion of fractions having these activities. Two groups of king penguins were constituted based on whether the birds preserved (histograms at left) or digested (histograms at right) their stomach contents during the fast.

At the quantitative level:
the microorganism inhibitory activities were higher in the "preservation" group compared to the "digestion" group at the beginning and the middle of fasting (FIG. 3). The distinction between the total and partial inhibitory activities shows that the difference between the two groups is linked to a larger proportion of total inhibitory activities in the "preservation" group compared to the "digestion" group—with this being true during the entire duration of fasting (FIG. 4).
the inhibitory activities (total and partial) were maintained during the entirety of fasting in the "preservation" group. A very strong decrease in the middle of fasting was seen in the "digestion" group.

Figure 5:
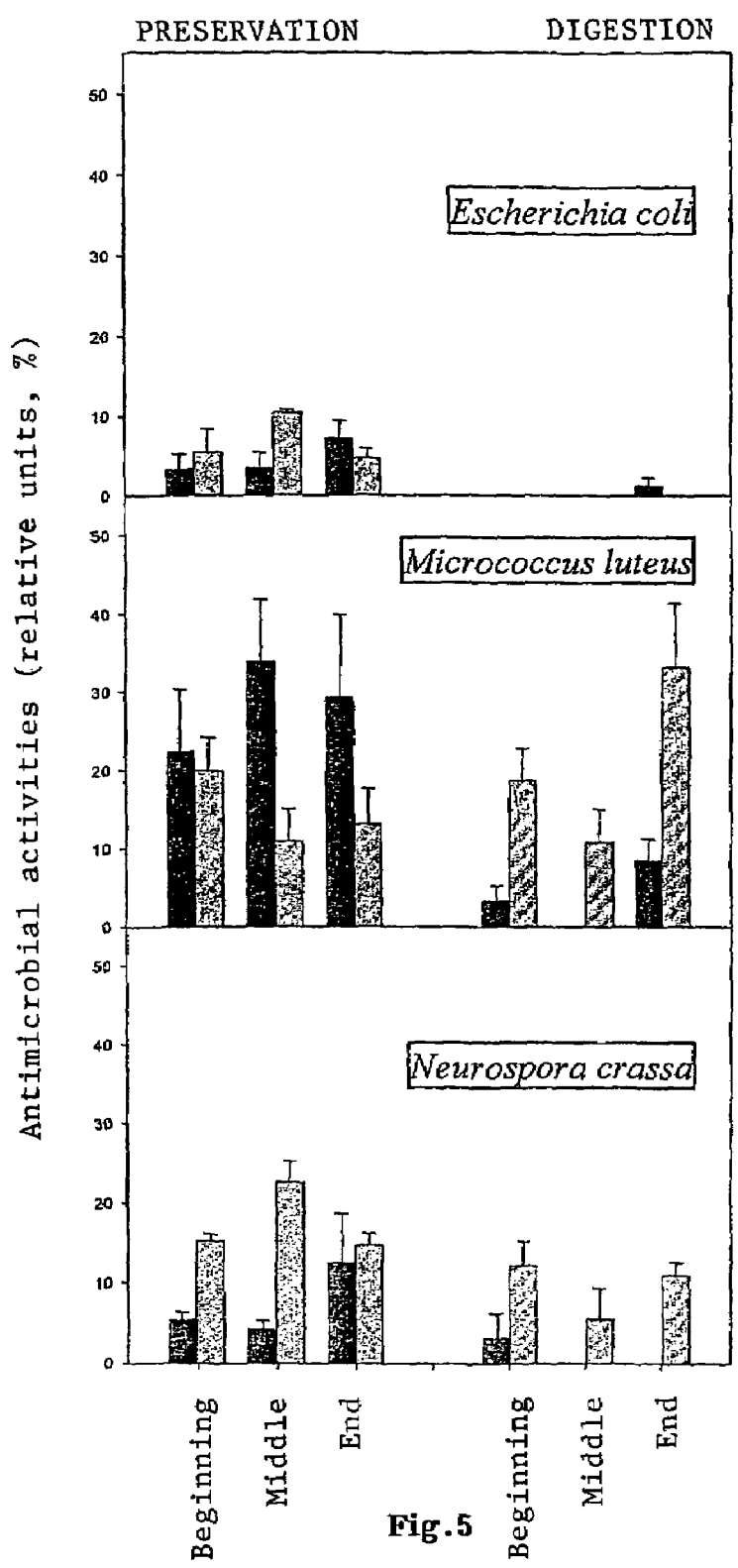
FIG. 5 is a graph showing the evolution of the antimicrobial activities against three types of microorganisms in the stomach contents of fasting king penguins incubating their eggs (see FIG. 4 for legends).

At the qualitative level (FIG. 5):
for all three types of microorganisms tested, the inhibitory activities were higher in the "preservation" group compared to the "digestion" group—with this being true during the entire duration of fasting. These activities were essentially directed against the Gram-positive bacterium tested (*M. luteus*).
with one exception, only the samples from the individuals of the "preservation" group had inhibitory activities against the Gram-negative bacterium tested (*E. coli*).

In conclusion, these results strongly support the implication of substances with antimicrobial activity in the phenomenon of preservation of the food bolus during incubation fasting of the male king penguin.

EXAMPLE 2

Isolation and Characterization of Antimicrobial Peptides from the Stomach Content Samples of Male King Penguins 2.1 Birds and Collection of Stomach Contents All of the stomach content samples were collected from male king penguins in their natural environment. The penguin colony was located on Possession Island (46°25'S-51°45' E) in the Crozet Island Archipelago. The samples were collected during the incubation period using a gastric probe. This study, performed in a protected zone and on a protected species, received the authorization of the French, Australian and Antarctic Territories (decision no. 2000-59 of Oct. 16, 2000) and the authorization of the Ministry of National Development and the Environment (authorization 00/240/AUT of Aug. 30, 2000).

a) Birds: The king penguin males were identified by means of a plastic ring placed temporarily on the flipper at the beginning of the incubation period just after the egg was laid and the passage of the egg between the female and the male.

The samplings of the stomach contents were performed during the last period of the incubation provided by the male. In order to perform an individual monitoring of the stomach contents, the samples were collected for each bird at three different stages of fasting: beginning, middle of fasting (approximately 7 days) and end of fasting. For the samplings at the beginning and the middle of fasting, the collection was performed while the bird was on its egg. For the final fasting stage, the male was captured just after he was relieved by the female outside of the colony.

The samples were collected in a calm situation outside of the colony. In order to limit the stress on the bird, it was placed in darkness by means of a hood. Similarly the egg was temporarily replaced by a heated plaster egg. The natural egg was placed in an incubator during sample collection. After the sample was collected, the bird was placed at the exact site of his capture. All of the birds studied brought the incubation to term.

Two groups of birds were formed based on whether they preserved ("preservation" group, n=3) or digested ("digestion" group, n=3) their stomach contents during incubation fasting.

b) Collection of the samples and storage: The stomach content samples were collected by a nondestructive, noninvasive method of intubation and aspiration. In order to obtain a homogeneous sampling, a quantity greater than required was collected in multiple steps, then immediately homogenized in a container kept in the freezer. It was only after this homogenization that sampling was performed. The samples were stored at $-80°$ C. During their shipment back to the French mainland, the samples were kept frozen successively at $-80°$ C. then in dry ice according to the transport technique (ship then airplane) prior to being again placed at $-80°$ C. until their analysis with a strict respect of the cold chain.

2.2 Extraction of the Hydrophobic Cationic Peptides and Prepurification

Extraction of the hydrophobic cationic peptides was performed on the frozen stomach content samples. The stomach content was ground using an ultraturax then an ultrasound probe in an extraction medium composed of trifluoroacetic acid (TFA, 0.2%) containing aprotinin (22.5 µg/ml final concentration) as protease inhibitor. The samples were maintained in the cold state in the freezer during the entire grinding step. The sample volume/extraction medium volume ratio was selected to be 1/10 at the end of grinding. The peptides were extracted at pH 2.5-3 under agitation overnight in a cold chamber. After centrifugation (10,000 rpm for 10 minutes at 6° C.), the supernatant was prepurified by extraction in solid phase on Sep-Pak $C_{18}$ Vac reversed phase cartridges (5 g of phase, Waters™). The cartridge was solvated with methanol and equilibrated with acidified water (0.05% TFA). The elution of the peptides/polypeptides and proteins was performed with an 80% solution of acetonitrile in acidified water. The eluted fraction was lyophilized prior to purification by high performance liquid chromatography (HPLC).

2.3 Purification of the Cationic Peptides a) Step 1. Purification on Semi-Preparative Column The 80% Sep-Pak fraction was subjected to chromatography on reversed phase support on a semi-preparative Aquapore RP-300 $C_{18}$ column (250×7 mm, Brownlee™), equilibrated with a 2% solution of acetonitrile in acidified water. The fractions were separated using a linear gradient of 2% to 72% of acetonitrile in acidified water in 70 minutes with a flow rate of 1.3 ml/minute.

This purification step was performed under controlled temperature (20-22° C.) on a Beckman Gold HPLC system equipped with a Beckman 168 photoarray detector. The molecules eluted from the column were detected by their absorbance at 225 nm.

The different fractions were collected manually, dried under vacuum (Speed-Vac, Savant) and reconstituted in 150 µl of ultrapure water (Millipore™) that had previously been filtered (Millipore™), prior to analysis of the antimicrobial activity.

b) Step 2. Purification on Analytic Column

Purification of the molecules with antimicrobial activity (total activity directed against the two strains of bacteria and the strain of filamentous fungi) was performed from a fraction stemming from the stomach content collected from a bird belonging to the "preservation" group at the end of fasting.

The second purification step was performed on an Aquapore OD-300 analytic column (220×4.6 mm, Brownlee™). The elution was performed by means of a biphasic acetonitrile gradient in acidified water from 2 to 23% in 10 minutes then from 23 to 38% in 45 minutes with a flow rate of 0.8 ml/minute. The different fractions were collected manually, dried under vacuum (Speed-Vac, Savant) and reconstituted in 70 µl of MilliQ water (Millipore™). In order to limit the use of the active product for the biological tests, only the Gram-negative strain E. coli was tested. The inactive fractions were then tested on N. crassa. No activity was detected, suggesting that the activity directed against the filamentous fungus N. crassa, recorded during the preceding purification, is clearly linked to the fraction having activity directed against the Gram-negative bacterium E. coli.

c) Step 3. Final Purification Phase on Analytic Column

The third purification step was performed on the same analytic column as in step 3 using as elution conditions a biphasic acetonitrile gradient in acidified water from 2 to 20% in 10 minutes and from 20 to 30% in 50 minutes with a flow rate of 0.8 ml/minute. The fractions were collected, dried under vacuum, taken up in 40 µl of water and analyzed for their antibacterial activity against E. coli.

These last two purification steps were performed under controlled temperature on a HPLC biocompatible system (all PEEK Waters, Waters model 626) linked to a variable absorbance detector (Waters 486). The molecules eluted from the column were detected by their absorbance at 225 nm and the antimicrobial activity was measured according to the procedure described in example 2.4 below.

2.4 Detection of Antimicrobial Activities

Antimicrobial activity was measured on four strains of microorganisms: *Micrococcus luteus* (Gram positive; collection of the Pasteur Institute, Paris), *Escherichia coli* SBS 363 (Gram negative; donated by M. Boquet of the Center for Nuclear Studies of Saclay), *Neurospora crassa* (filamentous fungus; fungus collection of the Clause Society, Paris) and *Candida albicans* (yeast; donated by Dr. Koenig, Hôpital Civil, Strasbourg). These four strains were selected from public or private collections because of their known sensitivity to natural antimicrobial peptides.

The bacteria to be tested were suspended in a suitable nutritive medium of the "poor broth" type corresponding to a solution of bactotryptone at 10 g/l with the addition of NaCl 5 g/l in ultrapure water.

The spores of the fungus N. crassa to be tested were suspended in a suitable culture medium of the "potato infusion—glucose" type. Preference was given to the use of 12 g of potato dextrose broth medium (1/2 PDB, Difco) per 1 liter of demineralized water. Two antibiotics were added to the culture medium: cefotaxime (final concentration at 100 µg/ml) and tetracycline (final concentration at 10 µg/ml).

The yeast strain C. albicans to be tested was incubated in a suitable culture medium of the "Sabouraud" type.

Antimicrobial activities were detected by a growth inhibition test in microtitration plates (Hétru and Bulet, 1997). One deposited 10 ml of each fraction collected in mictrotitration plates in the presence of 90 µl of culture medium containing the microorganisms (at a final concentration equivalent to 1 mDO at 600 nm).

For the bacteria and the yeast, incubation was performed at 30° C. for 12-24 h under agitation. The growth of the microorganisms was measured by monitoring the absorbance at 600 nm by means of a spectrophotometer reader of microtitration plates.

For the filamentous fungi, the incubation was performed at 37° C. in a humid atmosphere for 48 hours. The fungal growth was observed with a photon microscope after 24 h and quantified after 48 h by measurement of the absorbance at 600 nm by means of a spectrophotometer reader of microtitration plates.

2.5 Structural Characterization of the *Spheniscins*

2.5.1 Analysis by Mass Spectrometry

The purity and determination of the molecular mass of the bioactive molecules was performed by mass spectrometer using the technique called measurement of the time of flight after matrix-assisted laser ionization desorption (MALDI-TOF technique). The material used was a Brucker BIFLEX™ III mass spectrometer (Bremen, Germany) equipped with a SCOUT™ high resolution optic and a reflectron. This instrument has a maximum acceleration potential of 20 kV and can be used either in linear mode or in reflectron mode. Ionization was performed with a 337-nm beam emitted by a nitrogen laser at a frequency of 3 Hz. The mass spectra were calibrated externally with a standard mixture of *drosophila* peptides, i.e., drosocin, metchnikowin and drosomycin of known molecular mass respectively of 2199.5 Da, 3046.4 Da and 4890.5 Da (Bullet, 1999).

The sample to be analyzed was prepared according to the sandwich technique (Kussmann et al., 1997) displayed as follows: 0.5 µl of sample was deposited on a thin layer of α-cyano-4-hydroxycinnamic acid crystals (4-HCCA, Sigma) obtained by rapid evaporation of a saturated solution in acetone. The entire entity was covered with 0.5 µl of 4-HCCA matrix at saturation in a 50% solution of acetonitrile in water. After drying under a light vacuum, the sample was washed with 1.5 µl of TFA 0.1% before being dried again and introduced into the mass spectrometer.

Figure 7:
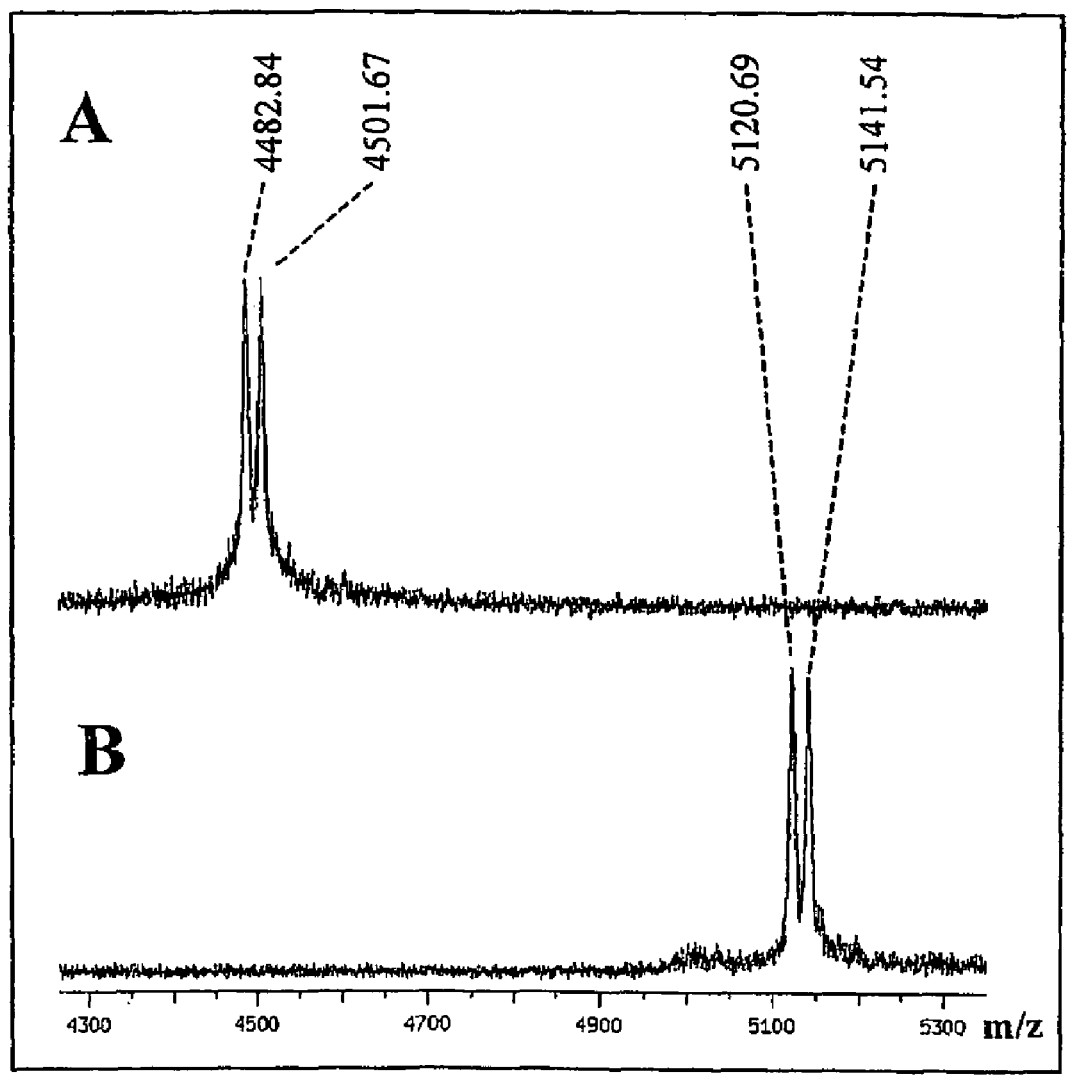
FIG. 7 is a graph showing the mass spectrum of the *spheniscins* in native form (A) and after reduction and pyridylethylation with the cysteine residues (B).

The mass spectrum obtained for the fraction isolated in step 3 of example 2.3 above is presented in FIG. 7A. This fraction contained two molecules of molecular mass in $MH^+$ at 4482.84 and 4501.67. The following step was to verify the presence of cysteine residues in the isolated antimicrobial molecules and possibly to modify these cysteine residues to promote the identification of the sequence during the peptide sequencing by Edman's degradation.

2.5.2 Verification of the Presence of Cysteine Residues and Determination of Their Number: Reduction and S-Pyridyl-ethylation a) Step 1: Chemical Treatment The presence of cysteine residues was determined after reduction and S-pyridylethylation. An aliquot fraction of the peptides purified in step 3 of example 2.3 was subjected to a chemical reduction step with 4 µl of dithiothreitol (final concentration 2.2 M) in 40 µl of Tris/HCl 0.5 M buffer, pH 8.3 containing 2 mM of EDTA and 6 M of guanidium chloride. The reaction medium was placed under a nitrogen atmosphere. After 60 minutes of incubation in the dark, 2 µl of 4-vinyl pyridine (alkylating agent) was added to the reaction. The reaction medium was placed under a nitrogen atmosphere and incubated for 10 minutes at 45° C. in the dark. The reaction was stopped by acidification with 50 µl of 10% TFA.

b) Step 2: Purification of the Reduced and Alkylated Peptides

The pyridylethylated peptides were purified from the reaction medium by reversed phase chromatography using a narrow bore $C_{1B}$ column (DeltaPak HPIC$_{1B}$, 2×150 mm, Waters™). Elution was performed by means of a linear gradient of acetonitrile in acidified water from 2 to 60% in 90 minutes with a flow rate of 0.2 ml/min. This separation was performed under controlled temperature on a biocompatible HPLC system (all PEEK Waters, Waters model 626) linked to a variable absorbance detector (Waters 486). The molecules eluted from the column were detected by their absorbance at 225 nm.

c) Step 3: Determination of the Number of Cysteine Residues by Mass Spectrometry Mass measurement of the pyridylethylated peptides was performed by a MALDI-TOF mass spectrometer according to the protocol presented in example 2.5.1. This fraction contained two molecules of molecular mass in MH$^+$ at 5120.69 and 5141.54 (FIG. 7B). The difference in molecular mass measured before and after reduction for the two molecules corresponded to the addition of six 4-vinyl pyridine residues (6×106 Da). This confirms the presence of six cysteine residues in the molecule at 4482.84 (m/z) and in that of 4501.67 (m/z) and their implication in the formation of three intramolecular disulfide bridges.

2.5.3 Determination of the Primary Sequences of the *Spheniscins* a) Step 1: Sequencing by Edman's Degradation

The automatic sequencing by Edman's degradation of the S-pyridylethylated peptides was performed on an ABI473A sequencer (Applied Biosystems Inc.). Two primary sequences of 38 amino acids, differing only by an amino acid in position 14 (histidine versus arginine), were obtained with an ambiguity regarding the amino acids in positions 31 and 37. The two peptides were treated with chymotrypsin to resolve this ambiguity.

b) Step 2: Digestion with Chymotrypsin and Analysis of the Chymotrypsin Fragments by Mass Spectrometry The fraction (4 μl) containing the S-pyridylethylated peptides was put in solution in 20 μl of Tris mM buffer at pH 7.8 containing 10 mM of $CaCl_2$ in the presence of chymotrypsin at the ratio of 1/20 (enzyme, peptides, weight/weight). Aliquot fractions (0.5 μl) were analyzed by MALDI-TOF mass spectrometry after 30 minutes and 55 minutes of incubation at 30° C. The samples were analyzed by MALDI-TOF mass spectrometry according to the protocol described in example 1.5.1. Among the chymotrypsin fragments observed after 55 minutes, one of the fragments with a molecular mass measured at 1261.05 (m/z) resolved the ambiguities seen after the sequencing by Edman's degradation. Identical C-terminals for both peptides.

The totality of the techniques employed thereby made it possible to obtain the complete structures of *spheniscin*-1 and *spheniscin*-2.

The primary sequence of *spheniscin*-1 is the following:

```
                                           (SEQ ID NO:1)
     SFGLCRLRRGFCAHGRCRFPSIPIGRCSRFVQCCRRVW
```

Calculated molecular mass: 4483.88 MH+

Measured molecular mass: 4482.84 MH+

The primary sequence of *spheniscin*-2 is the following:

```
                                           (SEQ ID NO:2)
     SFGLCRLRRGFCARGRCRFPSIPIGRCSRFVQCCRRVW
```

Calculated molecular mass: 4502.42 MH+

Measured molecular mass: 4501.67 MH+

Analysis of the protein and nucleotide databases (FASTA Genome, NCBI-TBLASTN) enabled demonstration that the *spheniscins* belonging to the family of β-defensins, antimicrobial peptides widely distributed in the animal world. A detailed comparison of the spheniscin sequences was performed with the sequences of the known β-defensins found in the epithelia of vertebrates, specifically in the chicken (*Gallus gallus*) and the guinea-fowl (*Meleagris gallopavo*). The homologies observed (FIG. 8) clearly show that the *spheniscins*, isolated from the stomach contents of king penguins, are clearly produced and secreted by the bird and do not stem from the food itself.

EXAMPLE 3

Evolution of the Spheniscins in the Stomach Contents Over the Course of the Incubation Fast in King Penguins 3.1 Detection of the *Spheniscins* in the Stomach Contents by MALDI-TOF Mass Spectrometry The analyses were performed for each stomach content sample on the fractions stemming from the first purification step (cf. example 2.3, step 1). The analysis procedure by MALDI-TOF mass spectrometry was that described in example 2.5.1.

All of the fractions originating from the first purification step stemming from the same individual in a given fasting stage and containing *spheniscin*-1 and/or *spheniscin*-2 were grouped together. The *spheniscins* were purified by successive chromatographies on suitable reversed phase columns using suitable acetonitrile gradients according to the model described above in example 2.3.

The purification steps were performed under controlled temperature on a biocompatible HPLC system (all PEEK Waters, Waters model 626) linked to a variable absorbance detector (Waters 486). The molecules eluted from the column were detected by their absorbance at 225 nm and the presence of *spheniscin*-1 and spehniscin-2 was confirmed by MALDI-TOF mass spectrometry.

3.2 Quantification and Evolution of the *Spheniscins* in the Stomach Contents Over the Course of the Incubation Fast in the King Penguin a) Step 1: Analysis by Zone Capillary Electrophoresis The first step enabling quantification of the *spheniscins* consisted of performing a zone capillary electrophoresis on a model 270 A-HT (Applied Biosystems Inc.). Four nl of each pool of fractions (12 μl) containing *spheniscin* (determined by MALDI-TOF mass spectrometry) were injected under assistance by the vacuum in a silica capillary (72 cm×50 μm). The analysis was performed in a citrate 20 mM buffer at pH 2.5. The electrophoresis was performed at 20 kV from the anode to the cathode for 20 minutes at 30° C. The migration was recorded at 200 nm. For each sample, the surface of the peak corresponding to *spheniscin*-1 and *spheniscin*-2 was determined.

b) Step 2: Quantification

So as to be able to implement quantification, the area of the peak obtained by capillary electrophoresis was compared to that of a calibrated solution of *spheniscins*. This solution corresponds to the sample analyzed by Edman's degradation. The precise quantity of *spheniscins* sequenced was determined by measurement of the repetitive yield and the initial yield obtained during the sequencing by Edman's degradation.

Figure 6:
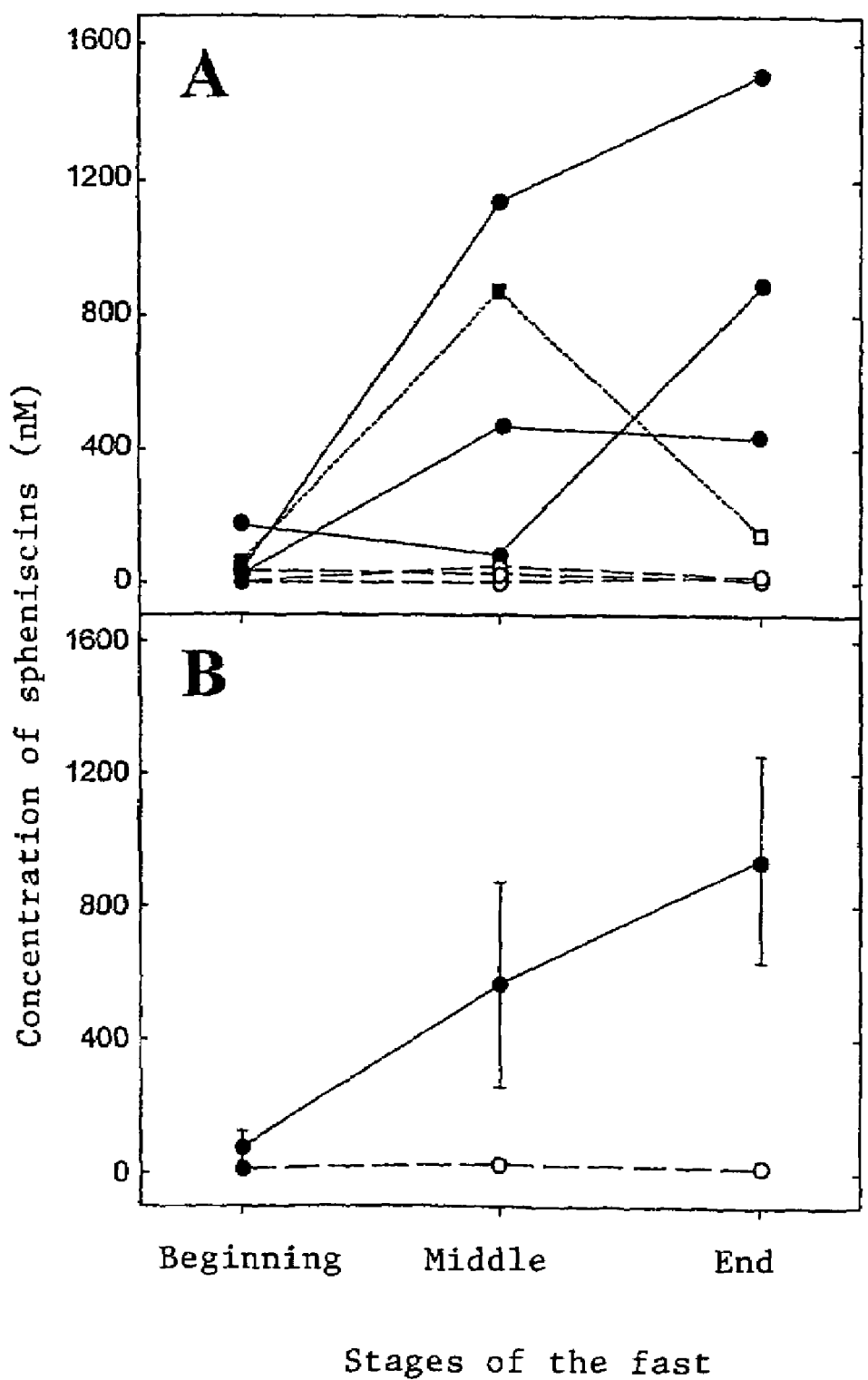
FIG. 6 is a graph showing the quantitative evolution of the spheniscins over the course of the fast in the stomach contents of fasting king penguins incubating their eggs. Two groups of king penguins were constituted based on whether the birds preserved (black circles and solid lines) or digested (white circles and large dashes) their stomach contents during the fast. The individual values (A) and the mean values±SDM (B) are shown. In (A) the values for an individual having preserved its stomach content between the beginning and the middle of the fast (black squares) then having digested it between the middle and the end of the fast (white squares) are also shown (small dashes).

The quantities observed were then brought to the concentrations present in the initial sample of the stomach content. The data obtained clearly showed a notable fluctuation in the content of *spheniscins* in the stomach contents between the two treated groups: the "preservation" and "digestion" groups (FIG. 6). Moreover, in the "preservation" group, a clear increase in the *spheniscin* levels was seen between the beginning and the end of the fast.

EXAMPLE 4

Synthetic Form of *Spheniscin-*2, its Antimicrobial Activity and Study of the Effect of the pH Value on its Functionality 4.1 Results We evaluated the antimicrobial properties as well as the secondary structure (three-dimensional, 3D) of the peptides (*spheniscins*). A synthetic peptide of composition and structure identical to one of the variants of the peptides of the invention, i.e., *spheniscin*-2, was produced chemically. Based on the synthetic *spheniscin*-2, the following were studied:

the spectrum of activity of *spheniscin*-2 on a large range of microorganisms including strains that are pathogenic for humans. Strains of Gram-positive and Gram-negative bacteria, yeasts and filamentous fungi were used.

the activity of *spheniscin*-2 as a function of the pH of the medium. In fact, in the case of the preservation of the alimentary bolus in the king penguin, it has been shown that the pH value varies between 4 and 6 (Thouzeau et al., 2003). The test was conducted in vitro to determine whether such a pH value could have an impact on the activity of *spheniscin* in vivo. This study was essential in the context of the potential use of these molecules for the preservation of foodstuffs or the fight against microbial infections in the gastrointestinal environment.

Figure 9:
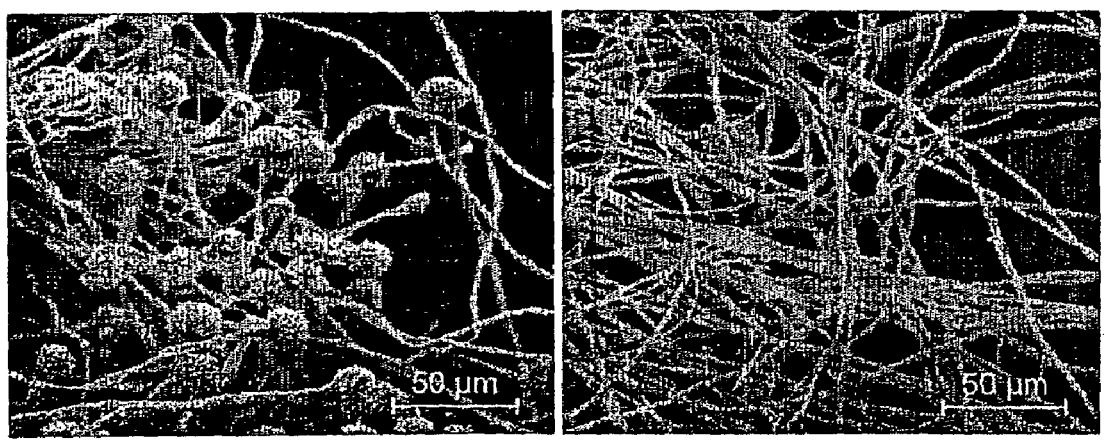
FIG. 9 shows the deleterious effect of *spheniscin*-2 on the growth of *Aspergillus fumigatus*, a pathogenic filamentous fungus (observation with electronic microscope (Philips XL30 LaB6)).

Five major results emerged from these two studies:

*Spheniscin*-2 strongly affects the growth of a large number of Gram-negative strains of bacteria (Table 1). This effect is principally of the bactericidal type (lysis of the bacterial cells);

*Spheniscin*-2 is also active against a large variety of Gram-negative strains of bacteria (Table 1). In contrast to that seen with the Gram-positive strains, this effect is primarily of the bacteriostatic type (termination of bacterial multiplication);

*Spheniscin*-2 possesses antifungal activity both against yeasts as well as against filamentous fungi (Table 1). This effect can be fungicidal (lysis of the spores) but can also affect the reproductive phase of the fungi by blocking sporulation as we could see on the human pathogen fungus *Aspergillus fumigatus*. This latter effect is shown in FIG. 9:

The existence of different modes of action of spheniscin depending on the microorganism strains affected by this peptide;

*Spheniscin-*2 is functional in the range of pH values observed in the stomach contents of the king penguin, i.e., from pH 4 to pH 6 (Table 2).

In conclusion, the demonstration of the broad spectrum of activity of *spheniscin*-2 affecting the growth of bacteria and fungi that are pathogens of plants and humans, and the maintenance of the functionality of this peptide at the pH values observed in vivo in the stomach are supplementary evidence in favor of the implication of substances with antimicrobial activity in the phenomenon of the preservation of the alimentary bolus during incubation fasting of the king penguin. These biological properties also are in favor of the use of these molecules for the antimicrobial fight in an environment in which the pH would be moderately acid.

The paragraphs below provide supplementary characteristics pertaining to the synthetic form of *spheniscin*-2, its spectrum of antimicrobial activity and the study of the effect of the pH value on its functionality.

4.2 Production of the Synthetic Form of *Spheniscin*-2

The study of the properties of *spheniscin*-2 required the availability of an adequate amount of peptide which was difficult to obtain from the king penguin stomach content extract. A synthetic from of *spheniscin*-2 was obtained from Laboratoire ALTERGEN (Schiltigheim, France). The *spheniscin*-2 was produced by chemical synthesis according to a procedure known in the art. After renaturation of the molecule under suitable conditions known in the art, the purity of the molecule and its identity with the native molecule were checked using the procedure described below:

a) Treatment of the crude synthesized product: The powder constituting the crude synthesized product was washed with reliquats of trifluoroacetic acid present with multiple successive washings using a 50% ACN solution; washings interspersed with a step of drying under vacuum (Speed-Vac, Savant) followed by a lyophilization step.

b) Verification of the molecular mass and the organization of the disulfide bridges: The identity of the synthetic product washed in this manner was verified and compared with that of the native molecule obtained from the stomach content. The molecular mass as well as the purity of the synthetic *spheniscin* were verified by mass spectrometry according to the time of flight measurement after matrix assisted laser ionization desorption (MALDI-TOF technique, see example 2.5.1 for the details of the technique). The arrangement of the disulfide bridges characteristic of the molecule (Cys1-Cys5, Cys2-Cys4, Cys3-Cys6) was verified by enzymatic cleaving with trypsin (Boehringer Mannheim, Germany) followed by a mass imprint by MALDI-TOF of the fragments stemming from this digestion.

The totality of the results obtained showed that the synthetic spheniscin was the same as the natural *spheniscin*-2 molecule both in terms of its primary structure as well as its arrangement of the disulfide bridges:

Natural *spheniscin*-2 (Sphe-2N) and synthetic *spheniscin*-2 (Sphe-2S):
Calculated molecular mass: 4502.42 MH$^+$
Measured molecular mass (Sphe-2N): 4501.67 MH$^+$
Measured molecular mass (Sphe-2S): 4502.71 MH$^+$
Pairing of the cysteines: Cys1-Cys5, Cys2-Cys4, Cys3-Cys6

Due to this strict identity, the synthetic spheniscin was used to carry out the studies of the biological properties of this molecule and study of the three-dimensional structure of this peptide.

4.3 Determination of the Spectrum of Activity of Spheniscin-2

The antimicrobial activities expressed in minimal inhibitory concentration (MIC) of spheniscin 2 (concentrations comprised between 0.2 µM and 100 µM) were determined against bacteria, yeasts and fungi using a growth inhibition test in liquid medium in microtitration plates (for the detailed protocol see example 2.4 as well as Hétru and Bulet, 1997).

The bactericidal or bacteriostatic effect of the peptide was determined by spreading on Petri dishes and counting the colonies present after 24 h of incubation.

The strains of microorganisms used were the same as certain ones previously described in the literature (Lowenberger et al., 1995, 1999) to which were added the following strains (donated by researchers): Bacillus cereus ATCC 11778 (Collection of the Pasteur Institute, Paris), Alcaligenes faecalis, Staphylococcus saprophyticus, S. haemolyticus and Nocardia asteroides (Professors Monteil and Piémont, Bacteriology Institute, University of Strasbourg, France), Escherichia coli SBS 363 (Dr. Boquet, Center of Nuclear Studies, Saclay, France), Vibrio metshnikovii and V. anguillarum (Dr. Bachère, IFREMER, Montpellier, France), Candida albicans IHEM 8060 (EntoMed, Strasbourg, France) and C. tropicalis (Dr. Koenig, Hôpital Civil, Strasbourg, France).

The control peptide MSI-94 was donated by Dr. M. A. Zasloff (Magainin Scientific Institute, Plymouth Meeting, Philadelphia) and the thanatin peptide was donated by Dr. Bulet (CNRS, UPR 9022, Strasbourg).

Table 1 below contains the spectra of activity of synthetic spheniscin-2 and two control peptides. The minimal growth inhibitory concentration (MIC) corresponds to the interval [a]-[b] in which [a] is the strongest concentration tested for which the microorganism grows and [b] is the weakest concentration tested starting at which there is 100% inhibition of growth of the microorganism (Casteels and Tempst, 1994). The control peptides were MSI-94 (a peptide of the mangainin family stemming from the skin of the batrachian Xenopus laevis and presenting a broad spectrum of antimicrobial activity; Maloy and Kari, 1995) for testing against the bacteria and yeasts; and thanatin (an antifungal peptide stemming from the insect Podisus maculiventris; Fehlbaum et al., 1996) for testing against the filamentous fungi. ND indicates that the activity of the peptide was not detected at the concentrations tested, i.e., up to the maximal concentration of 100 µM.

TABLE 1

Antimicrobial activity of synthetic spheniscin-2 and control peptides.
Ranges of concentrations tested: spheniscin-2 = 0.2 µM-100 µM;
MSI-94 (control for bacteria and yeasts) = 0.2 µM-10 µm;
thanatin (control for the fungi) = 0.4 µM-41.1 µM.

| Microorganism | MIC (µM) Spheniscin | Control antibiotic | Bactericidal effect of spheniscin-2 |
|---|---|---|---|
| Gram-positive bacteria | | | |
| Micrococcus luteus | 1.5-3 | 0.63-1.25 | Yes |
| Bacillus subtilis | 0.8-1.5 | 1.25-2.5 | Yes |
| B. cereus ATCC 11778 | 3-6 | 1.25-2.5 | Yes |
| B. megaterium | 0.4-0.8 | 0.31-0.63 | Yes |
| Staphylococcus aureus | 1.5-3 | 1.25-2.5 | Yes |
| S. saprophyticus | 1.5-3 | 0.63-1.25 | No |
| S. haemolyticus | 1.5-3 | 0.63-1.25 | Yes |
| Nocardia asteroides | 0.8-1.5 | 1.25-2.5 | Yes |
| Aerococcus viridans | 0.4-0.8 | 1.25-2.5 | — |
| Listeria monocytogenes | 6-12 | 2.5-5 | — |
| Gram-negative bacteria | | | |
| Escherichia coli SBS 363 | 0.8-1.5 | 1.25-2.5 | No |
| E. coli 1106 | 1.5-3 | 1.25-2.5 | Yes |
| Enterobacter cloacae | ND | 5-10 | — |
| Salmonella typhimurium | 6-12 | 2.5-5.0 | No |
| Klebsiella pneumoniae | 50-100 | 2.5-5.0 | No |
| Pseudomonas aeruginosa ATCC 82118 | 6-12 | 0.63-1.25 | No |
| Alcaligenes faecalis | ND | 2.5-5 | — |
| Vibrio metshnikovii NCTC 8483 | 25-50 | — | Yes |
| V. anguillarum ATCC 19264 | 25-50 | — | No |
| Yeasts | | | |
| Candida glabrata | >100 | ND | |
| C. albicans IHEM 8060 | 50-100 | 2.5-5.0 | |
| C. tropicalis | 1.5-3 | 2.5-5.0 | |
| Fungi | | | |
| Neurospora crassa | 3-6 | 2.0-4.0 | |
| Aspergillus fumigatus | 3-6 | close to 20 | |

ND: activity not detected in the range of concentrations tested.

4.4 Study of the Functionality of Spheniscin-2 at Different pH Values

The activity of the spheniscin was tested at pH values between 4.2 and 6.1 to determine whether the moderate acidity of the well preserved stomach content (pH 4-6; Thouzeau et al., 2003) could modify the efficacy of the spheniscin in vivo.

Strains of microorganisms capable of growing at such pH values were selected in advance: these were Pseudomonas aeruginosa and Escherichia coli 1106 (Gram-negative bacteria). The tests of antimicrobial activity were performed in liquid medium in microtitration plates (for the detailed protocol see example 2.4 as well as Hétru and Bulet, 1997). The pH of the liquid medium used was adjusted with hydrochloric acid for each test.

Table 2 below shows the effect of the pH value of the medium on the antimicrobial activity of synthetic spheniscin-2. Two strains of Gram-negative bacteria (Pseudomonas aeruginosa and Escherichia coli 1106) capable of growing in the range of pH values to be tested were selected. The range of pH values tested corresponded to the pH variations observed in the well preserved stomach content of the incubating king penguin (Thouzeau et al., 2003).

TABLE 2

Effect of the pH on the activity of synthetic spheniscin-2.

| Microorganism | pH | MIC (µM) after 48 h of incubation |
|---|---|---|
| Escherichia coli 1106 | 4.2 | 6-12 |
| | 5.2 | 25-50 |
| | 6.1 | 6-12 |
| | 7.2 | 1.5-3 |

TABLE 2-continued

Effect of the pH on the activity of synthetic spheniscin-2.

| Microorganism | pH | MIC (µM) after 48 h of incubation |
|---|---|---|
| Pseudomonas aeruginosa | 4.2 | >100 |
| | 5.2 | ND |
| | 6.1 | ND |
| | 7.2 | 6-12 |

ND: activity not detected in the range of concentrations tested

BIBLIOGRAPHIC REFERENCES

The subject matter of the following publications is incorporated herein be reference:

Bals, R., Goldman, M. J., & Wilson, J. M. (1998). Mouse beta-defensin 1 is a salt-sensitive antimicrobial 5 peptide present in epithelia of the lung and urogenital tract. *Infect Immun*, 66, 1225-32.

Bals, R., Lang, C., Weiner, D. J., Vogelmeier, C., Welsch, U., & Wilson, J. M. (2001). Rhesus monkey (*Macaca mulatta*) mucosal antimicrobial peptides are close homologues 10 of human molecules. *din Diagn Lab Immunol*, 8, 370-5.

Bals, R., Wang, X., Meegalla, R. L., Wattler, S., Weiner, D. J., Nehls, M. C., & Wilson, J. M. (1999). Mouse beta-defensin 3 is an inducible antimicrobial peptide expressed in the epithelia of multiple organs. *Infect Immun*, 67, 3542-7.

Bost, C. A., Georges, J.-Y., Guinet, C., Cherel, Y., Pitz, K., Charrassin, J.-B., Handrich, Y., Zorn, T., Lage, J., & Le Maho, Y. (1997). Foraging habitat and food intake of satellite-tracked king penguins during the autral 20 summer at Crozet Archipelago. *Marine Ecology Progress Series*, 150, 21-33.

Bulet, P. (1999). The antimicrobial peptides of *drosophila*. Medicine/sciences, 15,23-29.

Casteels, P., & Tempst, P. (1994) Apidaecin-type 25 peptide antibiotics function through a non-poreforming-mechanism involving stereospecificity. *Biochem Biophys Res Commun*, 199, 339-345.

Conejo-Garcia J. R. et al. Site internet Antimicrobial sequences databank (AMSDb) 30 http://www.bbcm.univ.trieste.it/-tossi/paql.htm Diamond, G., Jones, D. E., & Bevins, C. L. (1993). Airway epithelial cells are the site of expression of a mammalian antimicrobial peptide gene. *Proc Natl Acad Sci U S A*, 90, 4596-600.

Duits, L. A., Langermans, J. A., Paltansing, S., van der Straaten, T., Vervenne, R. A., Frost, P. A., Hiemstra, P. S., Thomas, A. W., & Nibbering, P. H. (2000). Expression of beta-defensin-1 in chimpanzee (*Pan troglodytes*) airways. *J 5 Med Primatol*, 29, 318-23.

Duits, L. A, et al. Site internet Antimicrobial sequences databank (AMSDb) http://www.bbcm.univ.trieste.it/-tossi/pagl.htm Fehlbaum, P., Bulet, P., Chernysh, S., Briand, 10 J. P., Roussel, J. P., Letellier, L., Hetru, C., & Hoffmann, J. A. (1996) Structure-activity analysis of thanatin, a 21-residue inducible insect defense peptide with sequence homology to frog skin antimicrobial peptides. *Proc Natl Acad Sci U S A*, 96, 1221-1225.

Garcia, J. R., Jaumann, F., Schulz, S., Krause, A., Rodriguez-Jimenez, J., Forssmann, U., Adermann, K., Kluver, E., Vogelmeier, C., Becker, D., Hedrich, R., Forssmann, W. G., & Bals, R. (2001). Identification of a novel, multifunctional beta-defensin (human beta-defensin 3) with specific antimicrobial activity. Its interaction with plasma membranes of *Xenopus oocytes* and the induction of macrophage chemoattraction. *Cell Tissue Res*, 306, 257-6 4.

Garcia, J. R., Krause, A., Schulz, S., Rodriguez-Jimenez, F. J., Kluver, E., Adermann, K., Forssmann, U., Frimpong-Boateng, A., Bals, R., & Forssmann, W. G. (2001). Human beta-defensin 4: a novel inducible peptide with a specific salt—sensitive spectrum of antimicrobial activity. *FASEB J*, 15, 1819-21.

Gauthier-Clerc, M., Le Maho, Y., Clerquin, Y., Bost, C.-A., & Handrich, Y. (2002). Seabird reproduction in an unpredictable environment: how king penguins provide their young chicks with food. *Marine Ecology Progress Series*, in press, Gauthier-Clerc, M., Le Maho, Y., Clerquin, Y., Drault, S., & Handrich, Y. (2000). Penguin fathers preserve food for their chicks. *Nature*, 408, 928-9.

Harder, J., Bartels, J., Christophers, E., & 5 Schroder, J. M. (2001). Isolation and characterization of human beta-defensin-3, a novel human inducible peptide antibiotic. *J Biol Chem*, 276, 5707-13.

Harder, J., Bartels, J., Christophers, E., & Schroder, J. M. (1997). A peptide antibiotic from human skin. 10 *Nature*, 387, 861

Hétru, C., & Bulet, P. (1997). Strategies for the isolation and characterization of antimicrobial peptides of invertebrates. From *Methods in Molecular Biology*, vol. 78, W. M. Shafer (ed.) Humana Press Inc., Totowa, N.J.

Hiratsuka, T., Nakazato, M., Date, Y., Ashitani, J., Minematsu, T., Chino, N., & Matsukura, S. (1998). Identification of human beta-defensin-2 in respiratory tract and plasma and its increase in bacterial pneumonia. *Biochem Biophys Res Commun*, 249, 943-7.

Huttner, K. M., Brezinski-Caliguri, D. J., Mahoney, M. M., & Diamond, G. (1998). Antimicrobial peptide expression is developmentally regulated in the ovine gastrointestinal tract. *J Nutr*, 128, 297S-299S.

Huttner, K. M., Kozak, C. A., & Bevins, C. L. (1997). The mouse genome encodes a single homolog of the antimicrobial peptide human beta-defensin 1. *FEES Lett*, 413,45-9.

Jia, H. P., Wowk, S. A., Schutte, B. C., Lee, S. K., Vivado, A., Tack, B. F., Bevins, C. L., & McCray, P. B. Jr. (2000). A novel murine beta -defensin expressed in tongue, esophagus, and trachea. *J Biol Chem*, 275, 33314-20.

Jones, D. E., & Bevins, C. L. (1992). Paneth cells of the human small intestine express an antimicrobial peptide gene. *J Biol Chem*, 267, 23216-25.

Kussmann, M., Nordhoff, E., Rahbek-Nielsen, H., Haebel, S., Rossel-Larsen, M., Jakobsen, L., Gobom, J., Mirgorodskaya, E., Kroll-Kristensen, A., Palm, L.,& Roepstorff P. (1997). Matrix-assisted Laser Desorption/Ionization Mass Spectrometry Sample Preparation Techniques. Designed for Various Peptide and Protein Analytes. *J Mass Spectrom*, 32, 593-601.

Lowenberger, C., Bulet, P., Charlet, M., Hetru, C., Hodgeman, B., Christensen, B. M., & Hoffmann, J. A. (1995) Insect immunity: isolation of three novel inducible antibacterial defensins from the vector mosquito, *Aedes aegypti*. *Insect Biochem Mol Biol*, 25, 867-73.

Lowenberger, C., Charlet, M., Vizioli, J., Kamal, S., Richman, A., Christensen, B. M., & Bulet, P. (1999) Antimicrobial activity spectrum, cDNA cloning, and mRNA expression of a newly isolated member of the cecropin family from the mosquito vector *Aedes aegypti*. *J Biol Chem*, 274, 20092-20097.

Mac Cormack, W. P., & Fraile, E. R. (1990). Bacterial flora of newly caught antarctic fish *Notothenia neglecta*. *Polar Biology*, 10, 413-417.

Maloy, W. L., & Kari, U. P. (1995) Structure-activity studies on magainins and other host defense peptides; *Biopolymers*, 37, 105-122.

Mathews, M., Jia, H. P., Guthmiller, J. M., Losh, G., Graham, S., Johnson, G. K., Tack, B. F., & McCray, P. B. J. (1999). Production of beta-defensin antimicrobial peptides by the oral mucosa and salivary glands. *Infect Immun*, 67, 2740-5.

Minn, I., Kim, H. S., & Kim, S. C. (1998). Antimicrobial peptides derived from pepsinogens in the stomach of the bullfrog, *Rana catesbeiana*. *Biochim Biophys Acta*, 1407, 31-9.

Moore, K. S., Bevins, C. L., Brasseur, M. M., Tomassini, N., Turner, K., Eck, H., & Zasloff, M. (1991). Antimicrobial peptides in the stomach of *Xenopus laevis*. *J Biol Chem*, 266, 19851-7.

Morrison, G. M., Davidson, D. J., & Dorin, J. R. (1999). A novel mouse beta defensin, Defβ2, which is 5 upregulated in the airways by lipopolysaccharide. *FEBS Lett*, 442, 112-6.

O'Neil, D. A., Cole, S. P., Martin-Porter, E., Housley, M. P., Liu, L., Ganz, T., & Kagnoff, M. F. (2000). Regulation of human beta-defensins by gastric epithelial cells in response to infection with *Helicobacter pylori* or stimulation with interleukin-1. *Infect Immun*, 68, 5412-5.

Perregaux, D. G., Bhaysar, K., Contillo, L., Shi, J., & Gabel, C. A. (2002). Antimicrobial Peptides Initiate IL-ibeta Posttranslational Processing: A Novel Role Beyond Innate Immunity. *J Immunol*, 168, 3024-32.

Schonwetter, B. S., & et al. (1995). Epithelia antibiotics induced at sites of inflammation. *Sciences*, 265, 1645-1648.

Schroder, J. M. (1999). Epithelial antimicrobial peptides: innate local host response elements. *Cell Mol Life Sci*, 56, 32-46.

Soucek, Z., & Mushin, R. (1970). Gastrointestinal bacteria of certain antarctic birds and mammals. *Applied Microbiology*, 20, 561-566.

Tarver, A. P., Clark, D. P., Diamond, G., Russell, J. P., Erdjument-Bromage, H., Tempst, P., Cohen, K. S., Jones, D. E., Sweeney, R. W., Wines, M., Hwang, S., & Bevins, C. L. (1998). Enteric beta-defensin: molecular cloning and characterization of a gene with inducible intestinal epithelial cell expression associated with *Cryptosporidium parvum* infection. *Infect Immun*, 66, 1045-56.

Thouzeau, C., Froget, G., Monteil, H., Le Maho, Y. & Harf-Monteil, C. (2003) Evidence of stress in bacteria associated with long-term preservation of food in the stomach of incubating king penguins (*Aptenodytes patagonicus*). *Polar Biol*, 26, 115-123.

Wang, Y., Knoop, F. C., Remy-Jouet, I., Delarue, C., Vaudry, H., & Conlon, J. M. (1998). Antimicrobial peptides of the brevinin-2 family isolated from gastric tissue of the frog, *Rana esculenta*. *Biochem Biophys Res Commun*, 253, 600-3.

Yamaguchi, Y., Fukuhara, S., Nagase, T., Tomita, T., Hitomi, S., Kimura, S., Kurihara, H., & Ouchi, Y. (2001). A novel mouse beta-defensin, mBD-6, predominantly expressed in skeletal muscle. *J Biol Chem*, 276, 31510-4.

Zhang, G., Wu, H., Shi, J., Ganz, T., Ross, C. R., & Blecha, F. (1998). Molecular cloning and tissue expression of porcine beta-defensin-1. *FEBS Lett*, 424, 37-40.

Zhao, C., Nguyen, T., Liu, L., Shamova, O., Brogden, K., & Lehrer, R. I. (1999). Differential expression of caprine beta-defensins in digestive and respiratory tissues. *Infect Immun*, 67, 6221-4.

Zhao, C., Nguyen, T., Liu, L., Sacco, R. E., Brogden, K. A., & Lehrer, R. I. (2001). Gallinacin-3, an inducible epithelial beta-defensin in the chicken. *Infect Immun*, 69, 2684-91.

The invention claimed is:

1. An isolated peptide comprising an amino acid sequence of formula (II):

(II)
(SEQ ID NO:27)

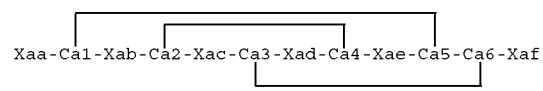

Xaa-Ca1-Xab-Ca2-Xac-Ca3-Xad-Ca4-Xae-Ca5-Ca6-Xaf wherein

Xaa is Ser-Phe-Gly-Leu, (SEQ ID NO:28)

Xab is Arg-Leu-Arg-Arg-Gly-Phe, (SEQ ID NO:29)

Xac is Ala-Xac2-Gly-Arg, (SEQ ID NO:33)

Xad is Arg-Phe-Pro-Ser-Ile-Pro-Ile-Gly-Arg (SEQ ID NO:30)

Xae is Ser-Arg-Phe-Val-Gln, and (SEQ ID NO:31)

Xaf is Arg-Arg-Val-Trp, (SEQ ID NO:32)

Xac2 is histidine or arginine, Ca1, Ca2, Ca3, Ca4, Ca5 and Ca6 are sulfur containing amino acids, wherein Ca1 is linked to Ca5, Ca2 is linked to Ca4 and Ca3 is linked to Ca6 and wherein the link is a disulfide bridge, and wherein the amino, acid sequence has antimicrobial activity.

2. A pharmaceutical composition comprising a therapeutically effective amount of an active agent comprising at least one peptide according to claim 1 and a carrier.

3. A food processing composition comprising an effective amount of a therapeutically effective amount of an active agent comprising at least one peptide according to claim 1 and a carrier.

4. An agricultural composition comprising a therapeutically effective amount of an active agent comprising at least one peptide according to claim 1 and a carrier.

5. The peptide according to claim 1, wherein Xac2 is arginine.

6. The peptide according to claim 1, wherein Xac2 is histidine.

7. The peptide according to claim 1, wherein Ca1, Ca2, Ca3, Ca4, Ca5 and Ca6 are cysteines.

8. The peptide according to claim 7, wherein Xac2 is arginine.

9. The peptide according to claim 7, wherein Xac2 is histidine.

* * * * *

UNITED STATES PATENT AND TRADEMARK OFFICE
CERTIFICATE OF CORRECTION

PATENT NO. : 7,384,911 B2  Page 1 of 1
APPLICATION NO. : 11/027111
DATED : June 10, 2008
INVENTOR(S) : Bulet et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 0 days Delete the phrase "by 0 days" and insert -- by 33 days --

Signed and Sealed this

Twenty-seventh Day of January, 2009

JOHN DOLL
*Acting Director of the United States Patent and Trademark Office*